United States Patent
Gregory et al.

(10) Patent No.: US 11,340,183 B1
(45) Date of Patent: May 24, 2022

(54) ULTRASENSITIVE, ULTRATHIN VAPOR SENSORS AND ARRAYS

(71) Applicant: PGR Holdings, LLC, Narragansett, RI (US)

(72) Inventors: Otto J. Gregory, Narragansett, RI (US); Peter P. Ricci, West Warwick, RI (US)

(73) Assignee: PGR Holdings, LLC, Narragansett, RI (US)

( * ) Notice: Subject to any disclaimer, the term of this patent is extended or adjusted under 35 U.S.C. 154(b) by 0 days.

(21) Appl. No.: 17/356,392

(22) Filed: Jun. 23, 2021

(51) Int. Cl.
  *G01N 25/48* (2006.01)
  *G01N 33/497* (2006.01)
  *A61B 5/08* (2006.01)
(52) U.S. Cl.
  CPC ......... *G01N 25/488* (2013.01); *G01N 33/497* (2013.01); *A61B 5/082* (2013.01); *G01N 2033/4975* (2013.01)
(58) Field of Classification Search
  CPC .... G01N 25/22; G01N 25/18; G01N 33/0037; G01N 33/0047; G01N 33/0054;
  (Continued)

(56) References Cited

U.S. PATENT DOCUMENTS 5,137,924 A   8/1992   Short et al.
5,731,510 A   3/1998   Jones et al.
(Continued)

FOREIGN PATENT DOCUMENTS

JP   2001250909 A   *   9/2001   ......... H01L 23/4985
JP   2017102131 A   *   6/2017
(Continued)

OTHER PUBLICATIONS

Daniel Mallin, "Increasing the Selectivity and Sensitivity of Gas Sensors for the Detection of Explosives" Master Thesis, University of Rhode Island, 2014. (Year: 2014).*

(Continued)

*Primary Examiner* — David A. Rogers
(74) *Attorney, Agent, or Firm* — Eversheds Sutherland (US) LLP; Christopher C. Bolten; Regis C. Worley, Jr.

(57) ABSTRACT

Ultrasensitive, ultrathin thermodynamic sensing platforms for the detection of chemical compounds in the vapor phase at trace levels are disclosed. Embodiments of the ultrathin vapor sensor comprise a substrate layer, an adhesion layer, a metallic microheater layer, and a catalyst layer. A sensor array may be provided including a plurality of sensors each having a different catalyst. When a sensor array exposed to an analyte, each of the various ultrathin vapor sensors of the array may experience an endothermic reaction, an exothermic reaction, or no reaction. A comparison of the reaction results to data comprising previously-obtained reaction results may be used to determine the presence and the identity of the analyte. Advantageously, these ultrathin vapor sensors utilize less power and provide greater sensitivity than known systems, and may be used to detect and identify analytes at the parts per trillion level. Specialized sensors configured to detect analytes falling into a certain category (e.g., explosives, drugs and narcotics, biomarkers, etc.) as disclosed, as well as general purpose sensors capable of detecting analytes from a plurality of categories.

28 Claims, 15 Drawing Sheets

(58) Field of Classification Search
CPC ........... G01N 33/0044; G01N 33/0042; G01N 33/004; G01N 33/0032; G01N 33/0031
See application file for complete search history.

(56) References Cited

U.S. PATENT DOCUMENTS

| | | | |
|---|---|---|---|
| 5,997,832 | A | 12/1999 | Lieber et al. |
| 6,171,378 | B1 | 1/2001 | Manginell et al. |
| 7,147,695 | B2 | 12/2006 | Mitra |
| 7,329,389 | B2 | 2/2008 | Horovitz et al. |
| 7,581,434 | B1 | 9/2009 | Discenzo et al. |
| 7,611,671 | B2 * | 11/2009 | Anvar ................. G01N 21/783 422/83 |
| 9,304,102 | B2 * | 4/2016 | Day ........................ C04B 35/01 |
| 9,518,970 | B2 * | 12/2016 | Burgi ................. G01N 33/0016 |
| 9,678,030 | B2 * | 6/2017 | Potyrailo ............ G01N 27/228 |
| 9,759,699 | B1 | 9/2017 | Gregory et al. |
| 10,272,434 | B2 | 4/2019 | Khattak et al. |
| 10,330,624 | B2 * | 6/2019 | Tayebi ................. G01N 27/124 |
| 10,416,140 | B2 * | 9/2019 | Von Waldkirch ........................... G01N 33/0031 |
| 11,041,838 | B2 * | 6/2021 | Rogers ................. G01N 27/125 |
| 2001/0003249 | A1 | 6/2001 | Stormbom |
| 2004/0241870 | A1 | 12/2004 | Miller et al. |
| 2005/0011260 | A1 | 1/2005 | Arndt et al. |
| 2005/0109621 | A1 | 5/2005 | Hauser et al. |
| 2005/0260453 | A1 | 11/2005 | Jiao et al. |
| 2006/0254501 | A1 | 11/2006 | Wang et al. |
| 2007/0028667 | A1 * | 2/2007 | Kim ................... G01N 33/0031 73/23.34 |
| 2007/0045114 | A1 * | 3/2007 | Wang ....................... C03C 3/091 204/431 |
| 2007/0105341 | A1 | 5/2007 | Sosnowchik et al. |
| 2008/0093226 | A1 | 4/2008 | Briman et al. |
| 2008/0148815 | A1 | 6/2008 | Lucas et al. |
| 2009/0218235 | A1 | 9/2009 | McDonald et al. |
| 2009/0235862 | A1 | 9/2009 | Cha et al. |
| 2009/0249859 | A1 | 10/2009 | Takahashi |
| 2010/0213603 | A1 | 8/2010 | Smeys et al. |
| 2011/0128828 | A1 | 6/2011 | Naniwa et al. |
| 2011/0149465 | A1 | 6/2011 | Hashimoto et al. |
| 2012/0041246 | A1 | 2/2012 | Scher et al. |
| 2012/0192623 | A1 | 8/2012 | Adami et al. |
| 2012/0297860 | A1 * | 11/2012 | Izawa ................. G01N 33/0013 73/31.05 |
| 2012/0301360 | A1 | 11/2012 | Meinhold et al. |
| 2014/0036953 | A1 | 2/2014 | Kimura et al. |
| 2014/0208828 | A1 * | 7/2014 | Von Waldkirch ........................... G01N 33/0031 73/25.05 |
| 2014/0212979 | A1 | 7/2014 | Burgi et al. |
| 2015/0316523 | A1 | 11/2015 | Patolsky et al. |
| 2018/0024089 | A1 * | 1/2018 | Mickelson ........... G01N 27/127 205/775 |
| 2018/0031532 | A1 * | 2/2018 | Lee ..................... G01N 33/0047 |
| 2018/0313800 | A1 * | 11/2018 | Rogers ............... G01N 33/0013 |
| 2020/0393432 | A1 * | 12/2020 | Swanson ................. G01N 27/14 |

FOREIGN PATENT DOCUMENTS

| | | | | |
|---|---|---|---|---|
| RU | | 2709051 C1 * | 12/2019 | |
| WO | WO-2019083939 A1 * | | 5/2019 | ........... A61B 5/1473 |

OTHER PUBLICATIONS

Aguilar, et al., "A Hybrid Nanosensor for TNT Vapor Detection," Nano Lett., 10:380-384 (2010).

Banerjee et al., "The Detection of Improvised Nonmilitary Peroxide Based Explosives Using a Titania Nanotube Array Sensor," Nanotechnology, 20—pp. 1-6 (Jan. 2009).

Buttigieg et al. "Characterization of the Explosive Triacetone Triperoxide and Detection by Ion Mobility Spectrometry," Forensic Science International 135:53-59 (Apr. 2003).

Campos et al. "An Electronic Tongue Designed to Detect Ammonium nitrate in Aqueous Solutions," Sensors, 13:14064-14078 (Oct. 2013).

Cho et al., "Colorimetric Sensors for Toxic and Hazardous Gas Detection: A Review," Electronic Materials Letters, 17:1-17 (Published Online Nov. 2020).

Choodum et al., "On-site semi-quantitative analysis for ammonium nitrate detection using digital image colourimetry," Science and Justice, 55:437-445 (May 2015).

Chu, et al., "Detection of Peroxides Using Pd/SnO2(subscript) Nanocomposite Catalysts," Sensors and Actuators B: Chemical, 197:376-384 (Jul. 2014).

Das et al. "Enhanced Response of Co-Planar MEMS Microheater-Based Methane Gas Sensor," IEEE Sensors Journal, 20(23):14132-14140 (Dec. 2020).

De Perre et al. "Rapid and specific detection of urea nitrate and ammonium nitrate by electrospray ionization time-of-flight mass spectrometry using infusion with crown ethers," Rapid Commun. Mass Spectrom., 26:154-162 (2012).

Diaz, et al., A Hybrid Nanosensor for TNT Vapor Detection, Nano Letters, 10(2):380-384 (Feb. 2010).

Dong et al., "Simulation of the columnar-to-equiaxed transition in directionally solidified Al-Cu alloys," Acta Materialia, 53:659-668 (2005).

Ewing et al., "A critical review of ion mobility spectrometry for the detection of explosives and explosive related compounds," Taianta, 54:515-529 (2001).

Ewing et al., "Direct Real-Time Detection of RDX Vapors Under Ambient Conditions," Anal. Chem., 85:389-397 (2013).

Ewing et al., "The vapor pressures of explosives," Trends in Analytical Chemistry, 42:35-48 (2013).

Germain et al., "Turn-on Fluorescence Detection of H2O2 and TAPT," Inorganic Chemistry, 47(21):9748-9750 (2008).

Gopalakrishnan et al., "Direct Detection of RDX Vapor Using a Conjugated Polymer Network," J. Am. Chern. Soc., 135:8357-8362 (May 2013).

Hampton, M., "Wanted: A Bomb Detector as Sensitive as a Dog's Nose," IEEE Spectrum, Oct. 11, 2019, https://spectrum.ieee.org/tech-talk/semiconductors/devices/using-a-twopronged-approach-to-detect-explosive-substances-from-bombs.

Hsueh et al. "A transparent ZnO nanowire MEMS gas sensor prepared by an ITO micro-heater," Sensors & Actuators B:Chemical, 304:127319 (2020).

Hwang et al., "Development of Micro-Heaters with Optimized Temperature Compensation Design for Gas Sensors," Sensors, 11:2580-2591 (Mar. 2011).

Hwang et al., "Gas sensing properties of SnO2 nanowires on micro-heater," Sensors & Actuators B: Chemical, 154:295-300 (2011).

Jung et al., "A low-power embedded poly-Si micro-heater for gas sensor platform based on a FET transducer and its application for NO2 sensing," Sensors & Actuators: B Chemical, 334:129642 (Feb. 2021).

Lee et al., "Highly Sensitive and Multifunctional Tactile Sensor Using Free-standing ZnO/PVDF Thin Film with Graphene Electrodes for Pressure and Temperature Monitoring," Scientific Reports, 5 (7887):1-8 (Jan. 2015).

Lin et al., "A Colorimetric Sensor Array for Detection of Triacetone Triperoxide Vapor," J. Am. Chem. Soc., 132 (44):15519-15521 (Oct. 2010).

Ma et al., "Ultrasensitive, Specific, and Rapid Fluorescence Turn-On Nitrite Sensor Enabled by Precisely Modulated Fluorophore Binding," Adv. Sci., 7:2002991 (1-11), (Nov. 2020).

Malashikhin et al., "Fluorescent Signaling Based on Sulfoxide Profluorophores: Application to the Visual Detection of the Explosive TATP," J. Am. Chern. Soc., 130:12846-12847 (Apr. 2008).

Moalaghi et al., "Tin oxide gas sensor on tin oxide microheater for high-temperature methane sensing," Material Letters, 263:127196, 4 pages (Mar. 2020).

Mullen et al., "Laser photoionization of triacetone triperoxide (TATP) by femtosecond and nanosecond laser pulses," International Journal of Mass Spectrometry, 252:69-72 (Feb. 2006).

(56) References Cited

OTHER PUBLICATIONS

Mullen et al., "Detection of Explosives and Explosives-Related Compounds by Single Photon Laser Ionization Time-of-Flight mass Spectrometry," Anal. Chem., 78(11):3807-3814 (Jun. 2006).

Rasanen et al., "Determination of gas phase triacetone triperoxide with aspiration ion mobility spectrometry and gas chromatography-mass spectrometry," Analytica Chimica ACTA, 623:59-65 (Jun. 2008).

Ricci et al., "Continuous Monitoring of TATP Using Ultrasensitive, Low-Power Sensors," IEEE Sensors Journal, 20(23):14058-14064 (Dec. 2020).

Ricci et al., "Sensors for the detection of ammonia as a potential biomarker for health screening," Scientific Reports, 11:7185 pp. 1-7 (Mar. 2021).

Ricci et al., "Free-standing, thin-film sensors for the trace detection of explosives," Scientific Reports, 11:6623, 10 pages (Mar. 2021).

Ricci et al., "Orthogonal Sensors for the Trace Detection of Explosives," IEEE Sensors Letters, 3(10):1-4 (Oct. 2019).

Rossi et al., "Trace Detection of Explosives Using Metal Oxide Catalysts," IEEE Sensors Journal, 19(13):4773-4780 (Jul. 2019).

Schulte-Ladbeck et al., "Determination of Peroxide-Based Explosives using Liquid Chromatography with On-Line Infrared Detection," Anal. Chem., 78(23):8150-8155 (Dec. 2006).

Schulte-Ladbeck et al., "Trace Analysis of Peroxide-Based Explosives," Anal. Chem., 75(4):731-735 (Feb. 2003).

Sigman et al., "Analysis of triacetone triperoxide by gas chromatography/mass spectrometry and gas chromatography/tandem mass spectrometry by electron and chemical ionization," Rapid Commun. Mass Spectrom., 20:2851-2857 (Jul. 2006).

Stambouli et al., "Headspace-GC/MS detection of TATP traces in post-explosion debris," Forensic Science International, 146S:S191-S194 (Dec. 2004).

Subramanian et al., "Cu—Pd (Copper-Palladium)," Journal of Phase Equilibria., 12(2):231-243 (1991).

Suematsu et al., "Pulse-Driven Semiconductor Gas Sensors Toward ppt Level Toluene Detection," Anal. Chem., 90:11219-11223 (Aug. 2018).

Sysoev, et al., Percolating SnO2 nanowire network as a stable gas sensor: Direct comparison of long-term performance versus SnO2 nanoparticle films, Sensors and Actuators B, 139(2):699-703 (Jun. 2009).

To et al., "Recent Developments in the Field of Explosive Trace Detection," ACS Nano., 14:10804-10833 (Aug. 2020).

Tong et al., "A fast response and recovery $H_2S$ gas sensor based on free-standing $TiO_2$ nanotube array films prepared by one step anodization method," Ceramics International, 43:14200-14209 (Jul. 2017).

Wang et al., "A Colorimetric Artificial Olfactory System for Airborne Improvised Explosive Identification," Adv. Mater., 32(14):1907043, 11 pages (Apr. 2020).

Wang et al., "A MEMS-based Air Flow Sensor with a Free-standing Micro-cantilever Structure," Sensors, 7(10):2389-2401 (Oct. 2007).

Wu et al., "Improved Selectivity and Sensitivity of Gas Sensing Using a 3D Reduced Graphene Oxide Hydrogel with an Integrated Microheater," ACS App. Mater. Interfaces, 7(49):27502-27510 (Dec. 2015).

Xu et al., "Surface Plasmon Resonances of Free-Standing Gold Nanowires Fabricated by Nanoskiving," Angew. Chem. Int. Ed., 45(22):3631-3635 (May 2006).

\* cited by examiner

| | Al$_2$CuO$_4$ | AZO | CrO$_2$ | CuO | CoO$_2$ | Fe$_2$O$_3$ | In$_2$O$_3$ | ITO | MnO | SnO | VO | WO |
|---|---|---|---|---|---|---|---|---|---|---|---|---|
| Optimal Operating Temperature (°C) | 250 | 250 | 175 | 175 | 175 | 175 | 175 | 175 | 250 | 175 | 200 | 250 |
| Acetone (10ppm) | − | + | − | − | − | − | + | + | − | + | + | − |
| H$_2$O$_2$ (7ppm) | + | + | − | − | − | − | + | − | + | − | + | + |
| TATP (20ppm) | NR | + | − | − | − | NR | + | − | NR | + | + | NR |
| DADP (50ppm) | − | + | − | − | − | NR | + | − | − | + | + | NR |
| 2,4-DNT (0.18ppm) | + | + | − | − | − | NR | + | + | + | + | + | + |

Legend: + Positive Response (Endothermic); − Negative Response (Exothermic); NR No Response

| | Al$_2$CuO$_4$ | Fe$_2$O$_3$ | ITO | CuO | SnO | WO |
|---|---|---|---|---|---|---|
| Optimal Operating Temperature (°C) | 250 | 175 | 175 | 250 | 175 | 250 |
| CBD (13ppt) | NR | + | + | - | + | + |
| Fentanyl (11ppt) | NR | NR | + | NR | + | NR |
| THC (0.15ppt) | - | - | + | - | + | + |

1800

| | Al$_2$CuO$_4$ | Fe$_2$O$_3$ | ITO | MnO | SnO | WO |
|---|---|---|---|---|---|---|
| Optimal Operating Temperature (°C) | 250 | 175 | 175 | 250 | 175 | 250 |
| Glucose (15ppt) | NR | NR | + | - | + | - |
| Fructose (15ppt) | NR | - | + | - | + | NR |
| Ammonia (7ppm) | NR | - | + | - | - | + |
| H$_2$O$_2$ (7ppm) | + | - | - | + | - | + |

1900 ⟶

| | Al$_2$CuO$_4$ | Fe$_2$O$_3$ | ITO | MnO | SnO | WO |
|---|---|---|---|---|---|---|
| Optimal Operating Temperature (°C) | 250 | 175 | 175 | 250 | 175 | 250 |
| Natural Gas (7ppm) | + | − | + | + | + | + |
| Acetone (10ppm) | − | − | + | − | + | − |
| Methanol (15ppm) | − | − | + | − | + | + |

Legend: + Positive Response (Endothermic); − Negative Response (Exothermic); NR No Response

ULTRASENSITIVE, ULTRATHIN VAPOR SENSORS AND ARRAYS

TECHNICAL FIELD

The present disclosure describes an ultrasensitive, ultrathin thermodynamic sensing platform for the detection of chemical compounds in the vapor phase at trace levels. This thermodynamic sensor platform may be referred to herein as an "ultrathin vapor sensor." The detection system described within has been used to detect chemical compounds, including explosives (including triacetone triperoxide (TATP) and dintrotoluene (DNT)), narcotics and drugs (including fentanyl and cocaine), hallucinogenic and non-hallucinogenic compounds (including cannabidiol (CBD) and tetrahydrocannabinol (THC)), biologics (including breath-based ammonia and hydrogen peroxide), agricultural VOCs (grapevine red-blotch disease) and other industrial compounds (including natural gas and propane).

BACKGROUND

Sensors utilizing microheaters have been shown to be effective in detecting explosives such as triacetone triperoxide (TATP) in the vapor phase at trace levels. Such sensors include those described in U.S. Pat. No. 9,759,699 to Gregory et al. and Chu et al., "Detection of Peroxides using $Pd/SnO_2$ Catalysts" published on 5 Jul. 2014 in Sensors and Actuators B: Chemical, the entire contents of each of which are incorporated herein by reference. While those sensors are extremely effective, it is desirable to provide sensors having increased sensitivity.

Those existing chemical sensors comprise relatively thick (measured in hundreds of micrometers) alumina substrates, relatively thick nickel films for the microheaters, and a thick passivation layer between the heater and the catalyst. Additionally, a temperature of approximately 500° C. is required to operate these sensors, and therefore a significant amount of power is required for the heaters. The relatively large thermal mass of the components of these sensors further adds to the required power to operate. Additionally, these sensors contained a substrate that was isotropic, which transferred heat laterally. This large thermal mass in combination with the lateral heat transfer was found to affect the accuracy of the heat measurements of the catalyst.

Other known sensors attempt to reduce the thermal mass. For example, sensors were manufactured having free-standing 25-micrometer nickel wire microheaters and no substrate. Such sensors demonstrated improved sensor response time and sensitivity. Nevertheless, these sensors had drastically reduced catalytic surface area, which limited their catalytic activity.

In view of the foregoing drawbacks of previously known systems, there exists a need for chemical sensors that operate at less than 500° C.

It further would be desirable to have chemical sensors that have a reduced thermal mass.

It further would be desirable to have chemical sensors that require less power to operate than some known systems.

It further would be desirable to have chemical sensors that are capable of detection of substances in extremely low concentrations.

SUMMARY

Provided herein are ultrathin, low power vapor sensors with extremely high sensitivity. Embodiments of the sensor operate at temperatures much lower than 500° C., have a reduced thermal mass, and use less power than known sensors. Moreover, embodiments of a ultrathin, low power vapor sensor in accordance with the present invention are highly sensitive and are capable of detecting chemicals at concentration levels as low as in parts per trillion (ppt).

In some preferred embodiments, the sensors comprise a Pd-based microheater deposited onto ultrathin (<40 μm thick) yttria-stabilized-zirconia substrate, which results in increased sensor sensitivity and selectivity over known devices. Embodiments of an ultrathin, low power vapor sensor display highly anisotropic thermal characteristics, which result in highly localized heating with corresponding improvements to the power efficiency. Embodiments of an ultrathin, low power vapor sensor have displayed the ability to detect one or more chemical compounds in the vapor phase at trace levels with relatively minimal power requirements.

In accordance with some aspects, a detection device is provided that includes at least one multi-layer sensor. In some embodiments, the sensor(s) has four layers. For example, the sensor may include a first layer having a substrate, a second layer in contact with the first layer, a third layer in contact with the second layer, and a fourth layer in contact with the third layer. The second layer may be an adhesion layer. The third layer may be a metallic microheater configured to receive power at a first power level to reach a setpoint temperature. The fourth layer may include a catalyst configured to undergo a chemical reaction when exposed to an analyte. The chemical reaction may be endothermic or exothermic. The metallic microheater may receive power at a second power level to maintain the setpoint temperature after the catalyst begins the chemical reaction. A heat effect indicative of information on the analyte may be determined by comparing the second power level to the first power level.

In some embodiments, the substrate is yttria-stabilized-zirconia. The adhesion layer may be copper. The metallic microheater may be palladium. The catalyst may be a metal oxide catalyst. The substrate may have a thickness of less than 40 micrometers.

The detection device may detect the analyte in a vapor phase based on the heat effect. The detection device may detect the analyte at concentration levels as low as in parts per trillion (ppt).

The detection device may include a controller configured to cause the power to be provided at the first power level to reach the setpoint temperature, to cause the power to be provided at the second power level to maintain the setpoint temperature after the catalyst begins the chemical reaction, and determine an existence, identity, and/or concentration of the analyte based on comparing the second power level to the first power level. As will be readily understood, the detection device may determine the existence, identity, and/or concentration of one or more additional analytes as well.

The detection device may include a reference sensor that is not coated with a catalyst. The detection device may include a second sensor having a second microheater in thermal communication with a second catalyst different from the first catalyst. The detection device may include third, fourth, and fifth sensors comprising third, fourth, and fifth catalysts, respectively.

In some embodiments, the first catalyst comprises aluminum copper oxide ($Al_2CuO_4$), the second catalyst comprises iron oxide ($Fe_2O_3$), the third catalyst comprises indium-tin oxide (ITO), the fourth catalyst comprises tin oxide (SnO), and the fifth catalyst comprises tungsten oxide (WO). The detection device may include a sixth sensor comprising a sixth catalyst selected from copper oxide (CuO) or manganese oxide (MnO).

In accordance with some aspects, a detection device is provided with an array of sensors that are electrically coupled to a controller. Each sensor in the array may have its own distinct catalyst such that reactions between an analyte(s) and the distinct catalysts (to the extent a reaction occurs) indicate information on the existence, identity, and/or concentration of the analyte(s). For example, the reactions may be thermal and the controller may monitor the variations in power applied to each sensor to determine the existence, identity, and/or concentration of the analyte(s). Each of the sensors in the array may be formed from the multi-layer configuration described above with its own distinct catalyst. A reference sensor may be included in the array that is formed in the multi-layer manner, but without a catalyst.

In some embodiments, a first sensor has a first microheater and a first catalyst in thermal communication with the first microheater and a second sensor has a second microheater layer and a second catalyst layer in thermal communication with the second microheater layer. The controller in electrical communication with the first sensor and the second sensor. The controller may cause power to be provided to the first and second sensors to heat the first sensor to a first setpoint temperature and to heat the second sensor to a second setpoint temperature, vary power applied to the first sensor and/or the second sensor to account for a thermal response caused by reactions between an analyte and the first catalyst layer and/or the second catalyst layer to maintain the first setpoint temperature and the second setpoint temperature, and determine an existence, identity, and/or concentration of the analyte based on the varied the power. The first setpoint temperature may be the same temperature as the second setpoint temperature.

In some embodiments, the detection device includes a reference sensor having a reference microheater and without a catalyst, the reference sensor in electrical communication with the controller. The detection device may include a third sensor comprising a third microheater and a third catalyst in thermal communication with the third microheater, a fourth sensor comprising a fourth microheater and a fourth catalyst in thermal communication with the fourth microheater, and a fifth sensor comprising a fifth microheater and a fifth catalyst in thermal communication with the fifth microheater. In some embodiments, the first catalyst comprises aluminum copper oxide ($Al_2CuO_4$), the second catalyst comprises iron oxide ($Fe_2O_3$), the third catalyst comprises indium-tin oxide (ITO), the fourth catalyst comprises tin oxide (SnO), and the fifth catalyst comprises tungsten oxide (WO). The detection device may include a sixth sensor comprising a sixth catalyst selected from copper oxide (CuO) or manganese oxide (MnO). As will be readily understood, the detection device may include more than six sensors and the additional sensors preferably have their own distinct catalyst.

In some embodiments, the first catalyst, the second catalyst, the third catalyst, the fourth catalyst, and the fifth catalyst each comprise aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO). The setpoint temperature may be between 50° C. and 500° C.

In accordance with some aspects, a method of detecting an analyte is provided. The method may include providing a sensor array comprising a first sensor and a second sensor, the first sensor comprising a first microheater layer and a first catalyst layer in thermal communication with the first microheater layer, the second sensor comprising a second microheater layer and a second catalyst layer in thermal communication with the second microheater layer; delivering power to the first and second sensors to heat the first sensor to a first setpoint temperature and to heat the second sensor to a second setpoint temperature; exposing the first and second sensors to an analyte such that the first catalyst layer and/or the second catalyst layer react with the analyte to generate a thermal response; varying power applied to the first sensor and/or the second sensor to account for the thermal response to maintain the first setpoint temperature and the second setpoint temperature; and/or determining an existence, identity, and/or concentration of the analyte based on varying the power.

Determining the existence, identity, and/or concentration of the analyte based on varying the power may include comparing the thermal response to a database of known thermal responses. The sensor array may include a reference sensor and determining the existence, identity, and/or concentration of the analyte may include analyzing information on power supplied to the reference sensor. In some embodiments, the first catalyst layer comprises aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO). In some embodiments, the second catalyst layer comprises aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO).

The detection device described herein may be used to detect a variety of analytes including but not limited to explosives (including triacetone triperoxide (TATP) and dintrotoluene (DNT)), narcotics and drugs (including fentanyl and cocaine), hallucinogenic and non-hallucinogenic compounds (including cannabidiol (CBD) and tetrahydrocannabinol (THC)), biologics (including breath-based ammonia and hydrogen peroxide), agricultural VOCs (grapevine red-blotch disease) and other industrial compounds (including natural gas and propane).

BRIEF DESCRIPTION OF THE DRAWINGS

FIG. 15 shows a summary table consisting of the thermodynamic sign indicative of the measured redox reactions, for 12 distinct catalysts making up an ultrathin vapor sensor array.

DETAILED DESCRIPTION OF THE PREFERRED EMBODIMENTS

Figure 1B:
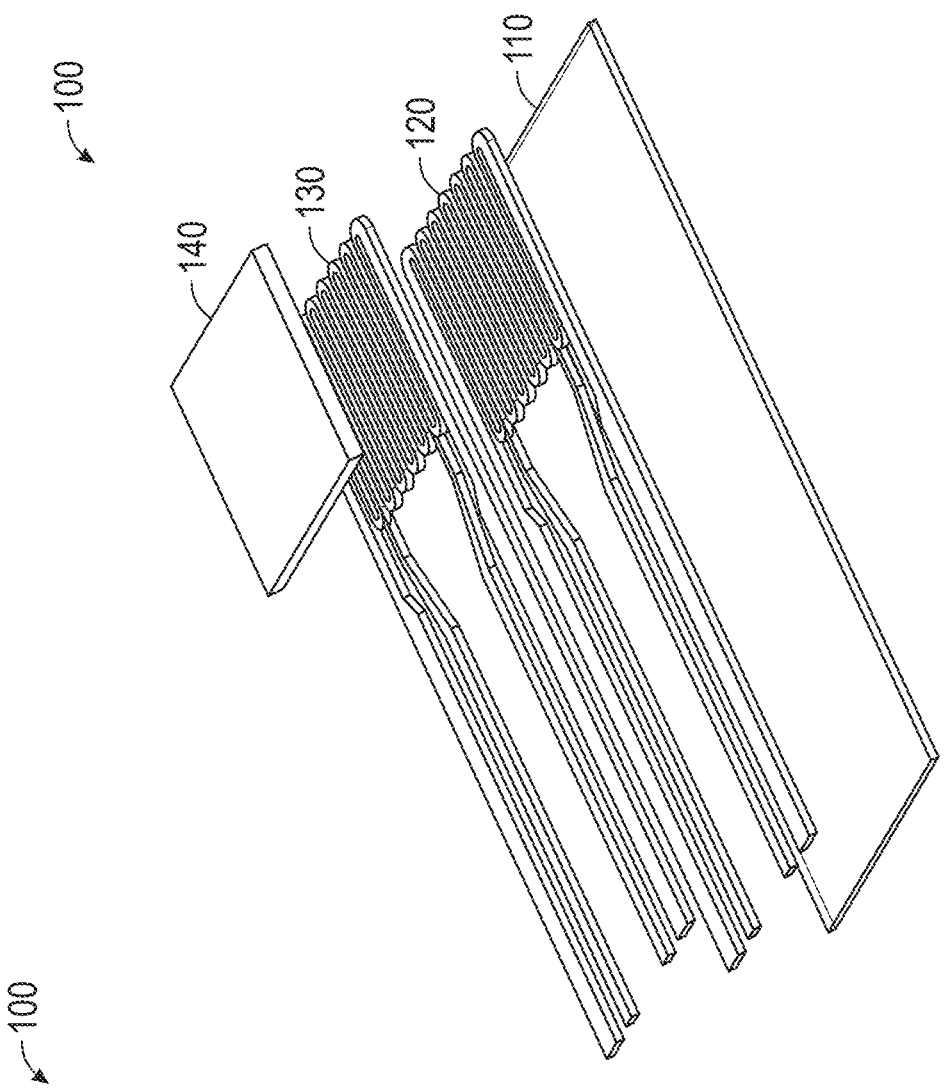
FIG. 1B shows an exploded view of an embodiment of a detection device.

Described herein are ultrathin vapor sensors utilizing thin film microheaters deposited onto ultrathin substrates, such as yttria-stabilized zirconia (YSZ) ceramic substrates. Embodiments of the present invention are capable of detecting trace levels of compounds in the gas phase. Embodiments of the ultrathin vapor sensors comprise at least two microheaters, one or more catalyst coated "active" microheaters and an uncoated "reference" microheater. The microheaters are thermally scanned over a selected temperature range and electrically powered, and preferably are configured to maintain a constant temperature. Upon reaching a set temperature, the power difference between the reference (uncoated) microheater and a catalyst coated microheater may be measured. This electrical power difference is the heat effect associated with oxidation/reduction reactions that occur on the surface of the catalyst after decomposition of a target molecule has occurred.

Measurement of the power difference between a sensor and the reference may be obtained utilizing a controller integrating Wheatstone bridge circuitry, or more preferably a half-Wheatstone bridge or an Anderson loop for increased efficiency. It will be appreciated that changes in the electrical power of the reference microheater and the catalyst coated microheater may be used to calculate the power difference and thus, the response of the sensor platform.

In operation of embodiments, the reference (uncoated) microheater and the catalyst coated microheaters are electrically powered to a predetermined setpoint temperature. Upon introduction of the analyte, the vapor sensor qualitatively or quantitatively measures the heat effect associated with interactions between the catalyst and the analyte. In general, oxidation reactions release heat, resulting in less electrical power required to maintain the same temperature and are therefore associated with negative responses. Conversely, reduction reactions absorb heat requiring more electrical power to maintain the same temperature and are therefore associated with positive responses. These heat effects are the result of oxidation/reduction reactions on the catalyst surface and the catalytic decomposition of the target molecule. The reference sensor is used to monitor sensible heat effects and other hydrodynamic effects, thus, mitigating false positives/negatives. As a result, the heat effect may be quantified, as well as qualified as endothermic, exothermic, or neither. Different catalysts used in different sensors in the detection system may experience a different heat effect when exposed to the same analyte. By comparing the quantitative or qualitative results from a plurality of sensors of a system to known results, the existence and concentration of an analyte may be determined.

The detection system described herein may be used to detect chemical compounds, including explosives (including triacetone triperoxide (TATP) and dintrotoluene (DNT)), narcotics and drugs (including fentanyl and cocaine), hallucinogenic and non-hallucinogenic compounds (including cannabidiol (CBD) and tetrahydrocannabinol (THC)), biologics (including breath-based ammonia and hydrogen peroxide), agricultural VOCs (grapevine red-blotch disease) and other industrial compounds (including natural gas and propane).

Experiments employing aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), and tin oxide (SnO) catalysts were performed. As a result of experiments using sensors comprising ultrathin YSZ ceramic substrates, the sensing mechanism was confirmed for a number of these analytes.

Reducing the thermal mass of the sensing platform further by utilizing ultrathin YSZ as the substrate for the thin film microheaters yielded some unexpected results. For example, the enhanced catalytic surface area (relative to freestanding wire sensors) combined with a reduced substrate thickness resulted in the ultrathin vapor sensor having a lower thermal mass without sacrificing catalytic surface area. In preferred embodiments of the present invention, the substrates are preferably thin YSZ substrates, such as 3 mol % YSZ having a thickness of between approximately 5 micrometers and 100 micrometers, more preferably between approximately 10 micrometers and 40 micrometers, and most preferably approximately 20 micrometers. The ultrathin YSZ substrate is preferably thermally anisotropic, so that the heat is highly localized in the "z" direction (perpendicular to the surface of the substrate). This result was more desirable than results seen with the alumina substrates used in known solid-state sensors, in which the heat is laterally spread. The thermal properties of embodiments of preferred embodiments are highly anisotropic in that the in-plane thermal conductivity of the YSZ (2.7 W/mK) is significantly lower than that of the alumina (30 W/mK). This difference causes the more of heat in ultrathin vapor sensors to remain in the area of catalyst, as compared to known systems employing alumina in which the heat without dissipates laterally to other areas of the sensor platform. As a result of this difference in heat transfer, there is a significant decrease in the temperature required for chemical detection, as well as a reduction in the power required to operate the sensor. For example, detection of compounds in the parts-per-million (ppm) and parts-per-billion (ppb) range is now possible at temperatures between 75° C. and 275° C. using embodiments of the ultrathin vapor sensors. Because more of the thermal energy is focused in the vicinity of the microheater and does not spread to other areas of the substrate as compared to previously-known systems, the resolution of the measurement of the inventive systems is also improved.

Figure 1A:
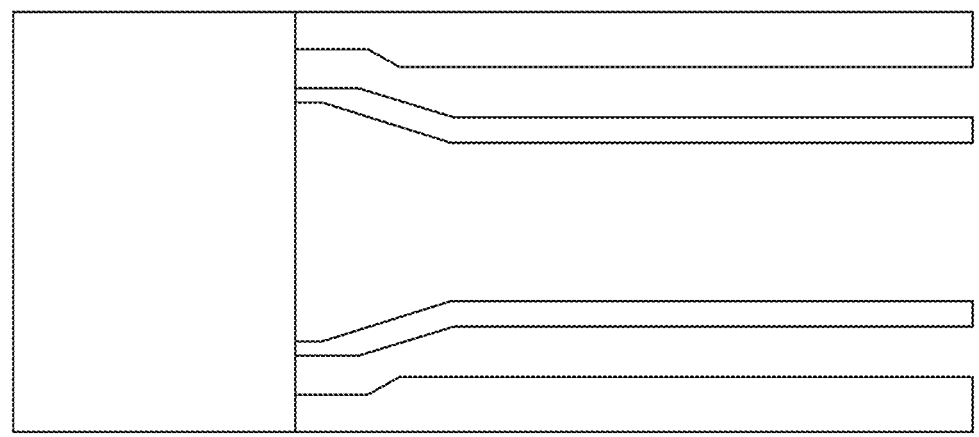
FIG. 1A shows a top view an embodiment of a detection device.

FIG. 1A and FIG. 1B show a top view of detection device 100, which may be an ultrathin vapor sensor, and an exploded view of detection device 100, respectively. As illustrated in FIG. 1B, detection device 100 may include multiple layers such as substrate layer 110, adhesion layer 120, microheater layer 130, and catalyst layer 140.

In preferred embodiments, substrate 110 is ultrathin YSZ substrate, which comprises a nominal thickness (e.g., 20 micrometers). Notably, layers of ultrathin vapor sensor 100 may have different thicknesses, and the films may be optimized for thickness to maximize surface area of the metal oxide catalyst while still maintaining the low mass characteristics of the microheater.

Adhesion layer 120 may be in contact with substrate layer 110 and microheater layer 130, as illustrated. Adhesion layer 120 may be formed of a metal such as copper. Adhesion layer 120 may have the same shape as microheater layer 130 as illustrated.

Microheater layer 130 may be formed of metal. Microheater layer 130 is designed maintain a setpoint temperature via the addition or reduction of heat upon exposure to an endothermic or exothermic chemical reaction, respectively, at catalyst layer 140. In some embodiments, microheater 130 is formed using photolithography to pattern a 1-micrometer thick palladium film microheater, which has considerably lower thermal mass than free-standing 25-micrometer diameter nickel wires used in previously-known sensors that have a much higher surface area. Palladium is a preferred choice for the metallization due to its catalytic amplification effect, which has been shown to improve sensitivity and response time.

Catalyst layer 140 is coated with a catalyst selected for detection of a predetermined analyte. The catalyst may be selected to chemically react with the analyte selected for detection.

Figure 1C:
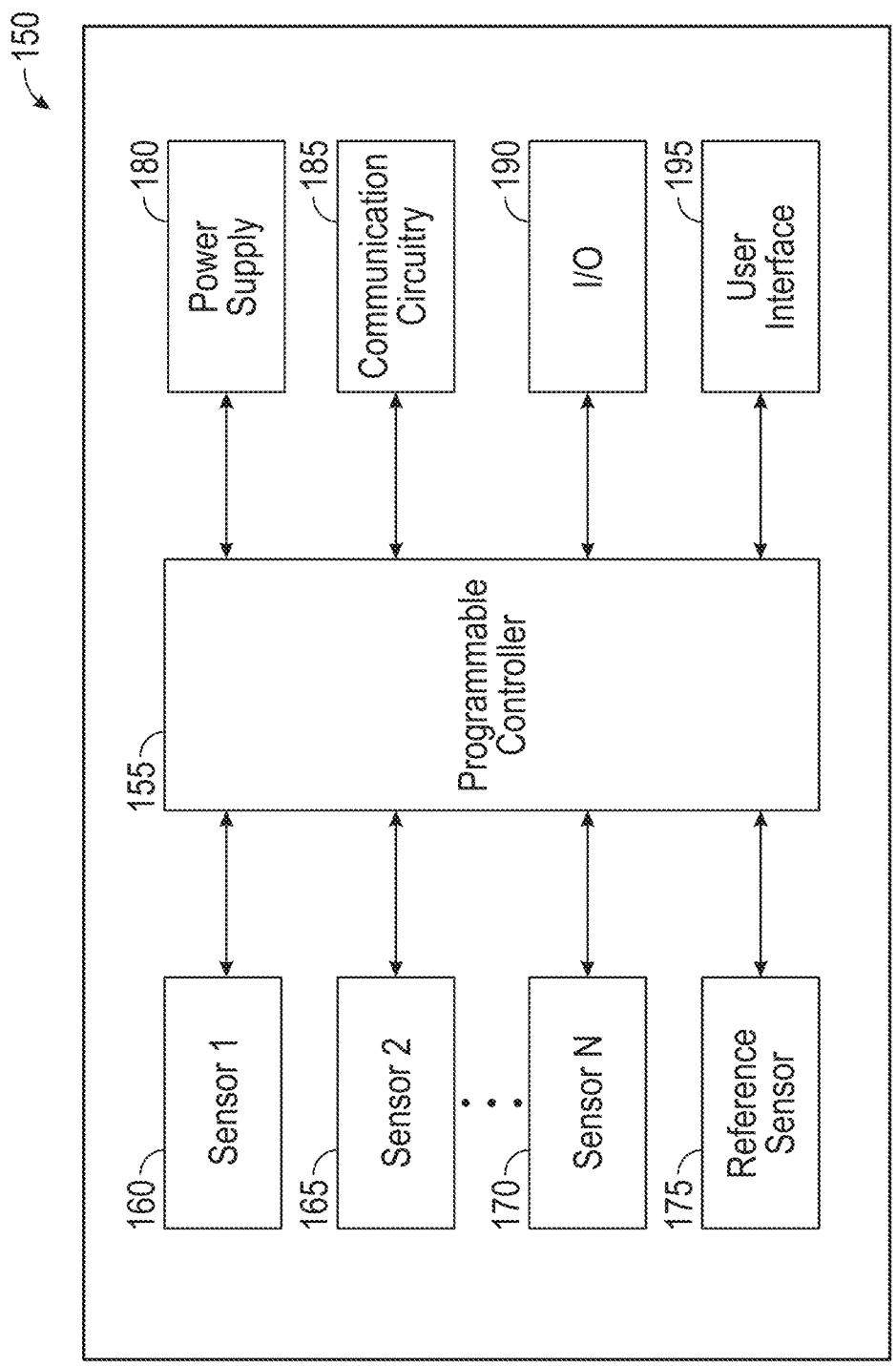
FIG. 1C shows a schematic diagram of an exemplary detection device.

FIG. 1C illustrates a generalized schematic diagram of the internal functional components of an exemplary detection device. Detection device 150 includes a plurality of sensors in communication with programmable controller 155. The plurality of sensors includes first sensor 160, second sensor 165, and so forth up to and including Nth sensor 170. Each of sensors 160, 165, 170 may be constructed in the manner described for the sensor in FIGS. 1A and 1B, although in some embodiments, each sensor has a different catalyst. Sensors also may include reference sensor 175, which may be constructed in the manner described for the sensor in FIGS. 1A and 1B, although the reference sensor preferably does not include a catalyst. Programmable controller 155 is in electronic communication with each of the plurality of sensors. Specifically, programmable controller 155 may provide a known amount of power to each of the plurality of sensors, though it will be appreciated that in some uses not all of the sensors will be necessary and in such cases programmable controller 155 may selectively provide power to the subset of the sensors that are necessary. Programmable controller 155 is configured to determine the amount of power provided to each of the sensors and to compare the power provided to any individual sensor (e.g., Nth sensor 170) to the power provided to reference sensor 175. Programmable controller 155 may integrate Wheatstone bride circuitry for each sensor, or more preferably a half-Wheatstone bridge or an Anderson loop for increased efficiency.

Detection device 150 further includes power supply 180, communication circuitry 185, input/output 190 and user interface 195, each of which are coupled to controller 155.

User interface 195 may be used to receive inputs from, and provide outputs to, a user. For example, user interface 195 may provide information to the user on the existence, identity, and/or concentration of an analyte detected by detection device 150. User interface 195 may include a power switch that completes a circuit between power supply 180 and controller 155 to selectively activate an operational mode of device 155. User interface 195 may include a setpoint temperature controller, wherein the user may select one or more operating temperatures for the plurality of sensors. User interface 195 may further include a volume control to selectively increase or decrease an audio output.

User interface 195 may include a touchscreen, switches, dials, lights, an LED matrix, other LED indicators, or other input/output devices for receiving inputs from, and providing outputs to, a user. In other embodiments, user interface 404 is not present on detection device 150, but is instead provided on a remote computing device communicatively connected to detection device 150 via the communication circuitry 185. User interface also may be a combination of elements on the detection device and a remote computing device.

Input and output circuitry (I/O) 190 may include ports for data communication such as wired communication with a computer and/or ports for receiving removable memory, e.g., SD card, upon which program instructions or data related to known reactions may be stored and/or for transmitting power to detection device 150. In one embodiment, I/O 190 comprises ports, and corresponding circuitry, for accepting cables such that controller 155 is electrically coupled to an externally located computer system.

Power supply 180 may supply alternating current or direct current. In direct current embodiments, power supply may include a suitable battery such as a replaceable battery or rechargeable battery and apparatus may include circuitry for charging the rechargeable battery, and a detachable power cord. Power supply 180 may be charged by a charger via an inductive coil within the charger and inductive coil. Alternatively, power supply 180 may be a port to allow device 155 to be plugged into a conventional wall socket, e.g., via a cord with an AC to DC power converter, for powering components within the device. Power supply 180 may be designed to supply power to the components of detection device 150. For example, power supply 180 may, responsive to instructions by controller 155, supply power to each of the sensors to maintain a setpoint temperature(s) and to vary the power supplied to each of the sensors to maintain the setpoint temperature(s) as the respective catalysts undergo thermal reactions with an analyte (if present).

Controller 155 includes electrical components and permits electrical coupling between controller 155 and sensors (e.g., first sensor 160, second sensor 165, N additional sensors 170, reference sensor 175) and other components, when included, such as communication circuitry 185, input/output 190, and user interface 195. Controller includes memory, which may be RAM, ROM, Flash, or other known memory, or some combination thereof. Controller preferably includes storage in which data may be selectively saved. For example, programmable instructions may be stored to execute algorithms for detecting the existence, identity, and/or concentration of an analyte based on the amount of power the controller causes to be supplied to each of the sensors in the array. The instructions may utilize information stored (e.g., in lookup tables) to determine information on the analyte. One or more electrical components and/or circuits may perform some of or all the roles of the various components described herein. Although described separately, it is to be appreciated that electrical components need not be separate structural elements. For example, controller 155 and communication circuitry 185 may be embodied in a single chip. In addition, while controller 155 is described as having memory, a memory chip(s) may be separately provided.

Controller 155 may be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A controller may also be implemented as a combination of computing devices, e.g., a combination of a DSP and a microprocessor, a plurality of microprocessors, one or more microprocessors in conjunction with a DSP core, or any other such configuration.

Controller 155 may contain memory and/or be coupled, via one or more buses, to read information from, or write information to, memory. The memory may include processor cache, including a multi-level hierarchical cache in which different levels have different capacities and access speeds. The memory may also include random access memory (RAM), other volatile storage devices, or non-volatile storage devices. The storage devices can include, for example, hard drives, optical discs, flash memory, and Zip drives.

Controller 155, in conjunction with firmware/software stored in the memory may execute an operating system, such as, for example, Windows, Mac OS, Unix or Solaris 5.10. Controller 155 also executes software applications stored in the memory. In one non-limiting embodiment, the software comprises, for example, Unix Korn shell scripts. In other embodiments, the software may be programs in any suitable programming language known to those skilled in the art, including, for example, C++, PHP, or Java.

Communication circuitry 185 is configured to transmit information, such as signals indicative of the presence, absence, and/or quantity of one or more target analytes, locally and/or to a remote location such as a server. Communication circuitry 185 is configured for wired and/or wireless communication over a network such as the Internet, a telephone network, a Bluetooth network, and/or a WiFi network using techniques known in the art. Communication circuitry 185 may be a communication chip known in the art such as a Bluetooth chip and/or a WiFi chip. Communication circuitry 185 may include a receiver and a transmitter, or a transceiver, for wirelessly receiving data from, and transmitting data to a remote computing device. In some such embodiments, the remote computing device may be a mobile computing device that provides the system with a user interface; additionally or alternatively, the remote computing device is a server. In embodiments configured for wireless communication with other devices, communication circuitry 185 may prepare data generated by controller 155 for transmission over a communication network according to one or more network standards and/or demodulates data received over a communication network according to one or more network standards.

In operation, detection device 100 may be exposed to an analyte such as a chemical compound. Upon exposure to the analyte, the catalyst of catalyst layer 140 may undergo a chemical reaction with the analyte, which may be an endothermic or exothermic reaction. Microheater layer 130 is exposed to any temperature change from the chemical reaction and demands increased power to maintain the setpoint temperature in response to an endothermic reaction and demands less power to maintain the setpoint temperature in response to an exothermic reaction at a rate related to the temperature change caused by the chemical reaction with the analyte that the detection device has been exposed to.

Figure 2:
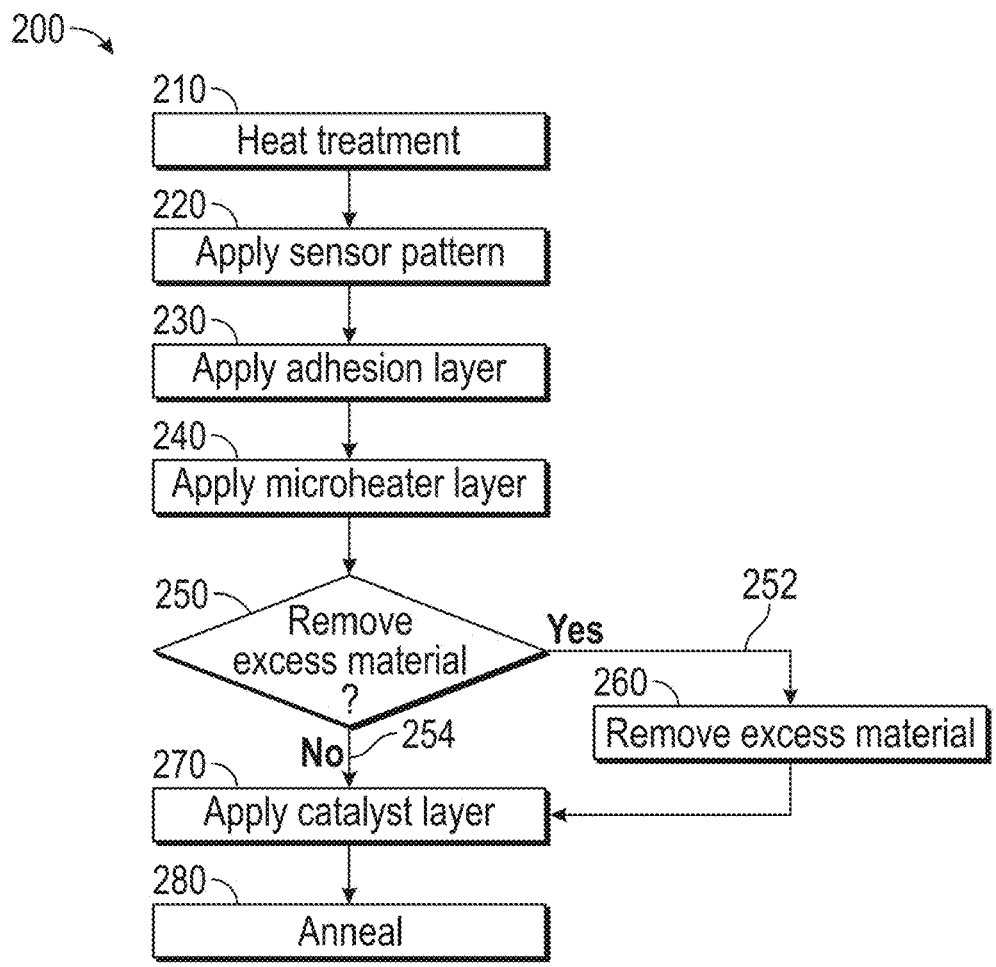
FIG. 2 shows a flowchart describing an exemplary fabrication procedure of an ultrathin vapor sensor.

Method 200 of forming an ultrathin vapor sensor in accordance with the present invention is illustrated in FIG. 2. The heat treatment step 210 involves heat treating a substrate. In preferred embodiments, the substrate is a YSZ substrate and the heat treatment occurs in ambient air at an elevated temperature (e.g., 1000° C.) over a period of time (e.g., three hours). At step 220, a sensor pattern is applied to the substrate in preparation for an adhesion layer. The pattern is preferably applied using photolithography or shadow masking, but it will be appreciated that other known techniques may be utilized. In preferred embodiments, the pattern includes a serpentine region in which portions of the pattern's path may remain close to other portions of the pattern's path. The pattern may be sinusoidal, zig-zag, irregular, a series of straight or curved segments, or other configuration that may be desired based on heat transfer characteristics, aesthetics, or other desirable characteristics. The adhesion layer is applied at step 230. Preferably, the adhesion layer is formed of a material such as copper applied at a thickness (e.g., 400 angstroms) over the thermodynamic sensor pattern. The adhesion layer may be applied using sputtering, evaporation, or other known techniques. At step 240, the metallic microheater layer is applied. In preferred embodiments, the microheater is formed of palladium and is applied at a thickness (e.g., 1 micrometer) over the pattern. Step 250 provides an optional decision as to whether it is desirable to remove excess material. If it is not desired, the method proceeds along path 254 to step 270. If it is desirable to remove excess material, such as if photolithography is utilized, then the method proceeds along path 252 to the step 260 wherein the extra material is removed. In some embodiments, optional step 260 involves lifting off excess copper and palladium metallization, leaving the remaining palladium-based sensor adhered to the YSZ substrate. Step 260 continues to step 270, wherein the catalyst layer is applied. In some preferred embodiments, a metal oxide catalyst is applied in a layer having a thickness (e.g., 1.2 micrometers) over the serpentine region of the palladium sensor. Proceeding to step 280, annealing is performed. In preferred embodiments, the copper-based microheater and palladium-based sensor are annealed at a temperature (e.g., 500° C.) for a period of time (e.g., 30 minutes) in a nitrogen atmosphere.

In developing embodiments of ultrathin vapor sensors in accordance with the present invention, a number of problems were identified and overcome. For example, YSZ substrates and palladium microheaters were found to exhibit different coefficients of thermal expansion (CTE), which led to poor adhesion as the sensor was heated and cooled during operation. This lack of adhesion was mitigated by sputter-coating a 400-angstrom thick copper adhesion layer in step 230. The copper adhesion layer was sputter-coated in the windows of the photoresist prior to deposition of the palladium microheater. Unlike known thermodynamic sensing platforms, the ultrathin vapor sensor does not require an $Al_2O_3$ passivation layer between the catalyst and the sensor. Removal of this layer further reduced the thermal mass by orders of magnitude relative to the alumina coatings employed in previous solid-state sensors which comprised an alumina cement layer with a thickness on the order of hundreds of micrometers. The excessive thermal mass associated with the alumina cement caused significant heat loss to the substrate, i.e., significant amounts of heat were dissipated before reaching the catalyst surface, thus producing a temperature gradient between the microheater and the catalyst surface. Removal of this passivation layer not only reduced the thermal mass of the sensor but also more effectively controlled the temperature of the catalytic layer, thereby improving the thermal resolution of the measurement when the catalyst interacted with an analyte. The catalyst layer preferably is a 1.2 μm thick metal oxide catalyst layer. As previously mentioned, a variety of catalysts have been experimentally investigated for this purpose. Each of these thin-film materials were sputter-coated onto the thin film resistor and optimized for thickness to maximize catalytic sensitivity while maintaining the low mass characteristics of the microheater. Overall, embodiments of the fully fabricated microheater comprise a thickness of approximately 21.6 micrometers.

Figure 3:
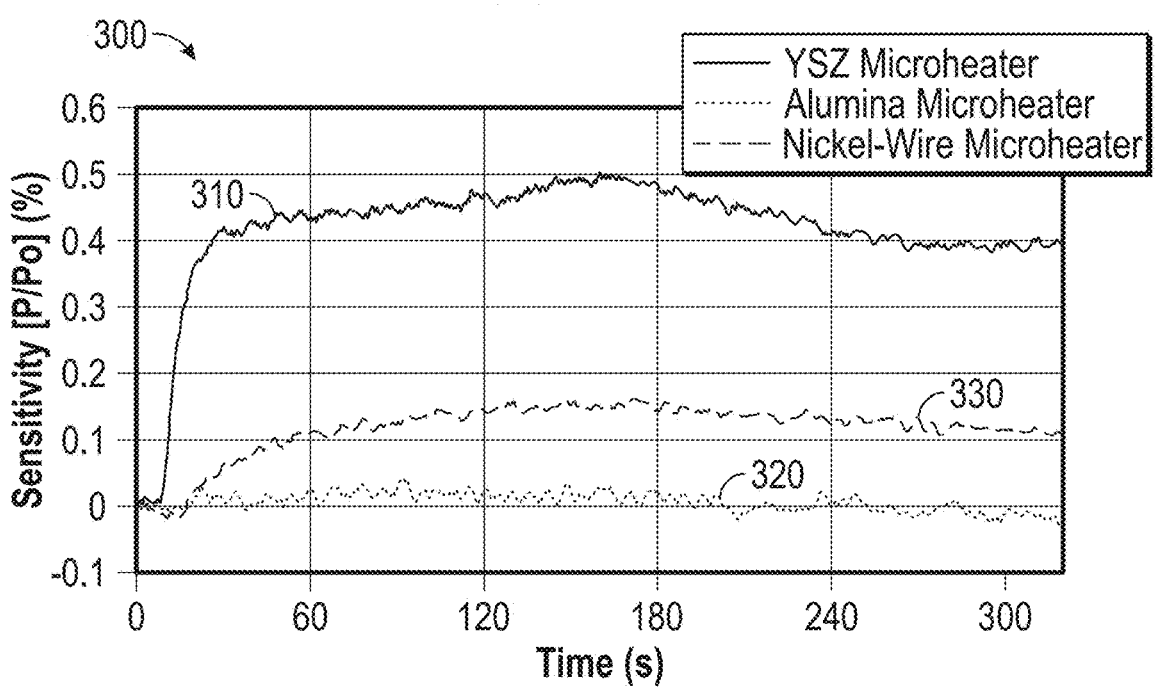
FIG. 3 shows an illustrative graphical representation of a comparison between the response of an ultrathin (YSZ-based) vapor sensor, an alumina-based sensor, and a freestanding nickel wire sensor to 20 ppm TATP using an operating temperature of 175° C.

A comparison of different sensors is made in reference to FIG. 3. As illustrated, FIG. 3 depicts comparison 300 between the sensitivity results of an YSZ-based embodiment of ultrathin vapor sensor 310 to both alumina-based sensor 320 and free-standing Ni-wire sensor 330. Each sensor platform employed a SnO catalyst and the target gas was 20 ppm triacetone triperoxide (TATP). The ultrathin vapor sensor utilizing the ultrathin YSZ substrates outperformed the Ni-wire microheaters in terms of both sensitivity and response time, e.g., the alumina-based sensor appeared unresponsive due to the relatively large operating powers required for heating (2-3 W). The ultrathin (YSZ-based) vapor sensor displayed a sensitivity of 0.45%, which is 2.5 times greater than the sensitivity of the free-standing Ni-wires. Additionally, the response time decreased significantly, which allowed real-time detection of the molecules of interest. The t10 response time of the YSZ-based sensor was approximately 10 seconds, which is significantly faster than the previous platforms (25 seconds for the alumina-based sensors and 17 seconds for the Ni-wire sensors). These results were attributed to a reduction in thermal mass with no corresponding sacrifice in the catalyst surface area.

Figure 4B:
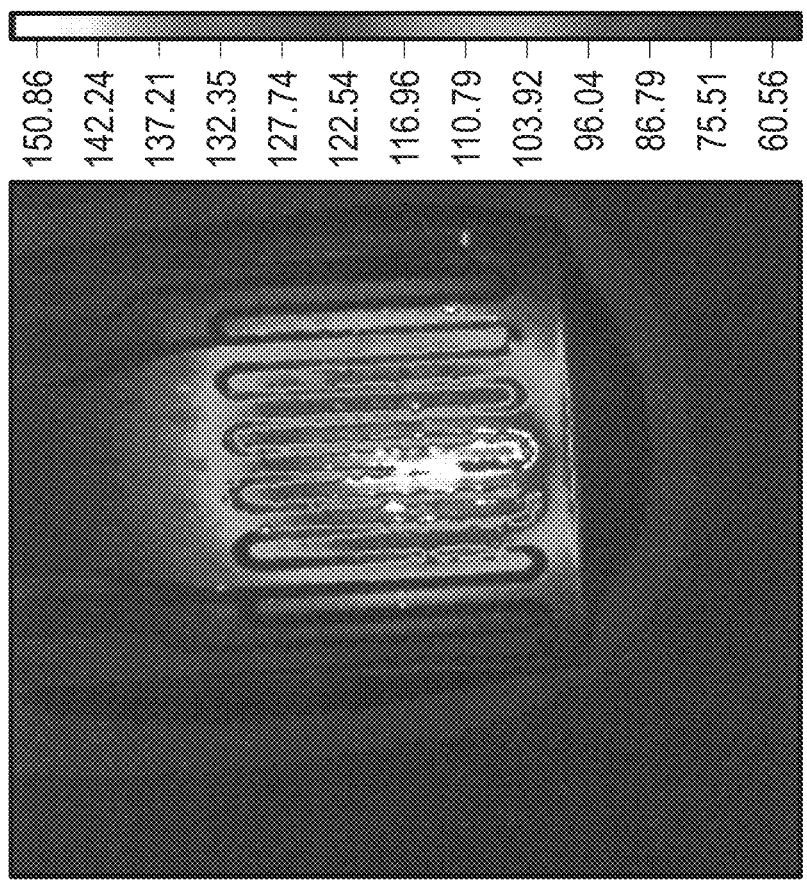
FIG. 4B shows a high-resolution IR image of an ultrathin (YSZ-based) vapor sensor employing a Ni microheater using an operating temperature of 175° C.
Figure 4A:
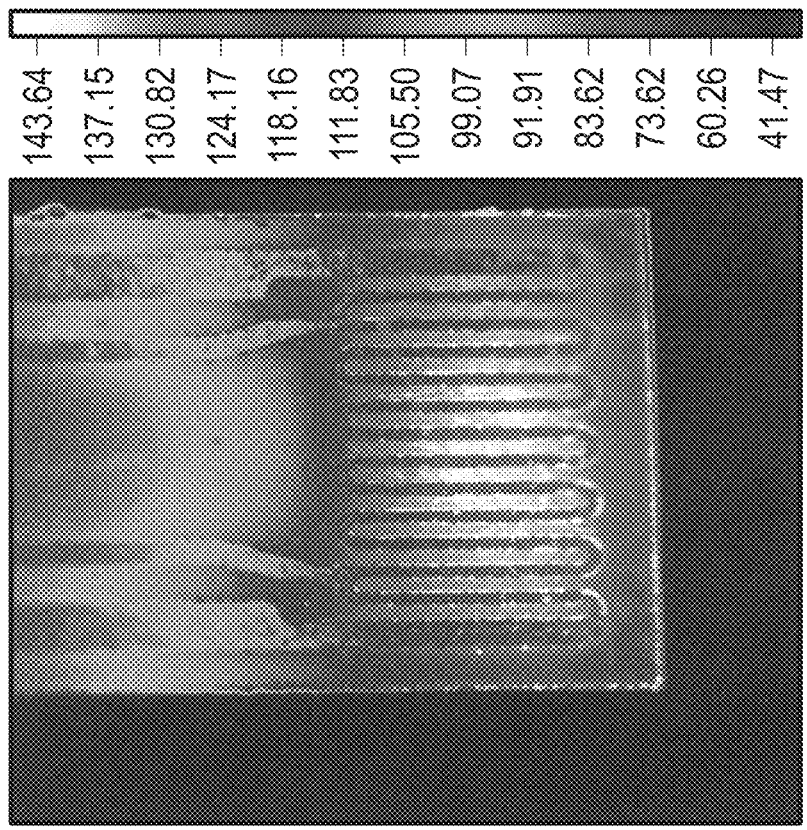
FIG. 4A shows a high-resolution IR image of a 1 mm thick alumina-based sensor employing a Ni microheater using an operating temperature of 175° C.

FIG. 4A depicts a high-resolution infrared (IR) image of a 1 mm thick alumina-based sensor, whereas FIG. 4B depicts a high-resolution IR image of an ultrathin (YSZ-based) vapor sensor. These figures illustrate the above-mentioned findings that the ultrathin YSZ substrate exhibits highly localized heating in the "z" direction when compared to the alumina based solid-state sensors. The thermal properties were found to be highly anisotropic in that the in-plane thermal conductivity of the YSZ (2.7 W/mK) was significantly lower than that of the alumina (30 W/mK). This difference caused the heat to remain in the area of catalyst without dissipating laterally to the rest of the sensor platform to the degree of the alumina based solid-state sensors. One outcome of this was a significant decrease in the temperature required for detection using the ultrathin vapor sensor, as well as a reduction in the power required to operate the sensor. In comparison, previously-known alumina-based sensors required operating temperatures of 500° C. or greater for the detection of compounds at trace levels. The YSZ-based sensor showed better sensitivity and response times at significantly lower operating temperatures (175° C.), which resulted in a significant decrease in power (400 mW). The YSZ-based microheaters also cooled to room temperature in just seconds after deactivation, thus making the overall duty cycle much shorter in duration. These features permit real-time detection with little to no delay related to sensor recovery.

Figure 5:
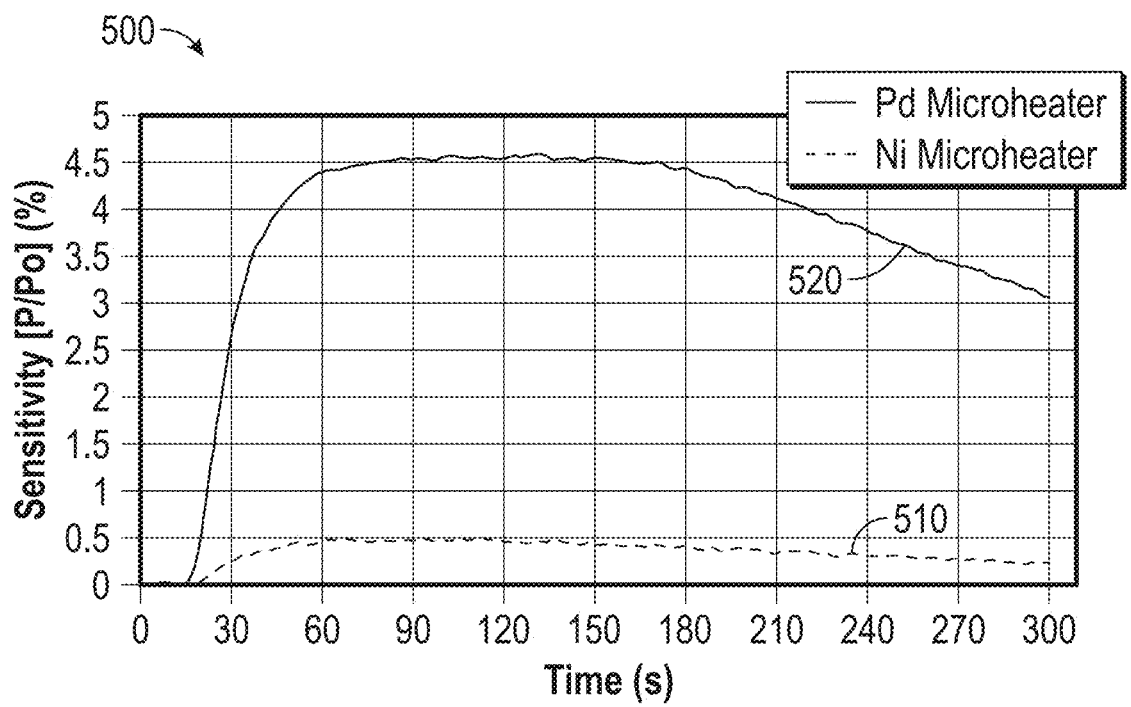
FIG. 5 shows an illustrative graphical representation of a comparison between the responses of two ultrathin (YSZ-based) vapor sensors to 20 ppm TATP. The sensors employed two different microheater metallizations using an operating temperature of 175° C.

Enhanced sensitivity of ultrathin vapor sensor embodiments as compared to known sensors can also be attributed to the implementation of a Pd-based microheater. FIG. 5 depicts comparison 500 between the response of an ultrathin vapor sensor employing a Ni-based microheater 510 and the response of an ultrathin vapor sensor employing a Pd-based microheater 520. The conditions of the comparison include 20 ppm TATP at 175° C. Even though the Pd thin films deposited on the YSZ were thick enough to be continuous, the catalytic properties of the Pd significantly increased the specific response of the SnO catalyst to TATP. The Pd-microheater sensors displayed a sensitivity of 4.5%, which represents an order of magnitude improvement over the Ni-based sensors. Due to the similar power requirements of the Pd-based microheaters (370 mW) and Ni-based microheaters (400 mW), the enhanced sensitivity was attributed to the heat effect observed for the Pd-based microheaters coated with a SnO catalyst. The observed catalytic amplification also reduced the response time of this sensor platform. The t10 response time of the Pd-based microheater was 8.75 s, which represents a substantial decrease relative to the Ni-based platform (10 s).

Figure 6:
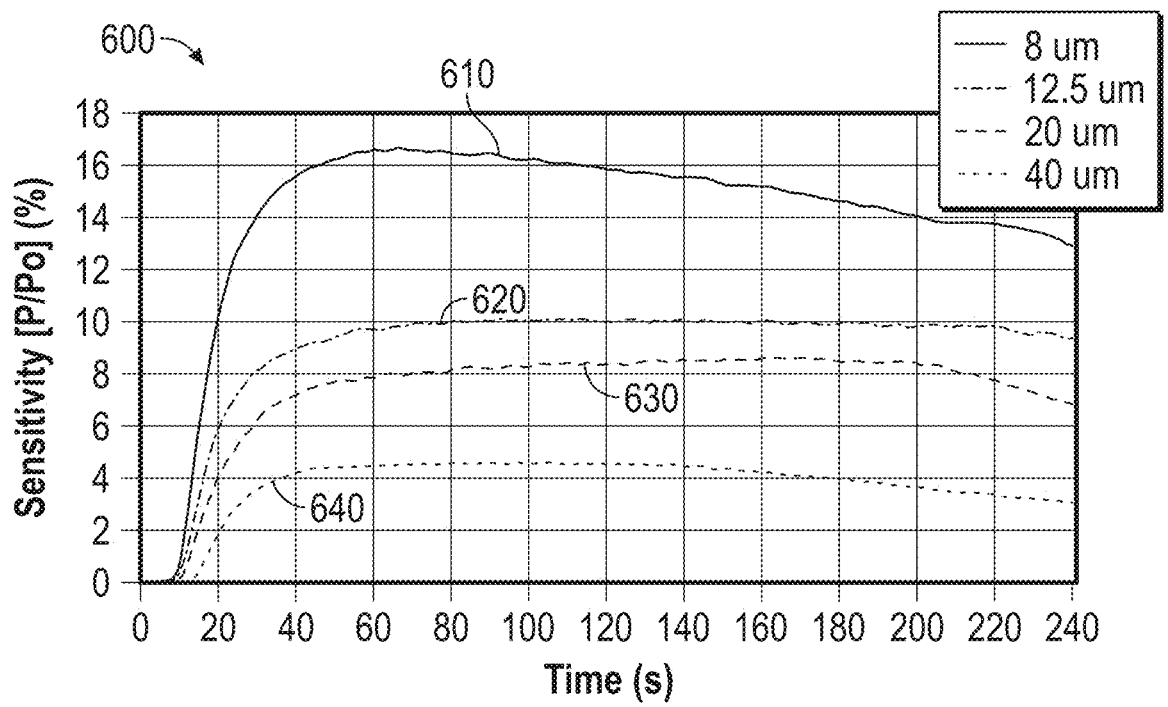
FIG. 6 shows an illustrative graphical representation of a comparison between the responses of four ultrathin vapor sensors fabricated on YSZ substrates of varying thickness to 20 ppm TATP using an operating temperature of 175° C.

Further improved performance of the ultrathin vapor sensor was achieved through the minimization of thermal mass. FIG. 6 depicts comparison 600 of the response times of four ultrathin vapor sensors fabricated on YSZ substrates of varying thicknesses when exposed to 20 ppm TATP. Specifically, comparison was made between results of 8 μm thick YSZ-based sensor 610, 12.5 μm thick YSZ-based sensor 620, 20 μm thick YSZ-based sensor 630, and 40 μm thick YSZ-based sensor 640. Empirical findings revealed that the sensitivity and response time improved as the thermal mass was reduced. Overall, an ultrathin vapor sensor employing 8 μm thick YSZ displayed the highest sensitivity of all sensors (16%), which represents a 30-fold increase in sensitivity over the 40 μm thick YSZ-based sensors. The reduction in thermal mass resulted in significantly lower power requirement as well. At an operating temperature of 175° C., the 8 μm thick YSZ sensors required only about 250 mW to operate, which represents a significant decrease over the 40 μm thick platform (370 mW). Additionally, much shorter response times were achieved through implementation of the 8 μm YSZ sensors, e.g., the Pd-based sensors fabricated on 8 μm YSZ required just 3 seconds to reach 10 percent of the maximum response. This improvement represents a 10-fold decrease over the alumina-based sensors (25 seconds).

Figure 7A:
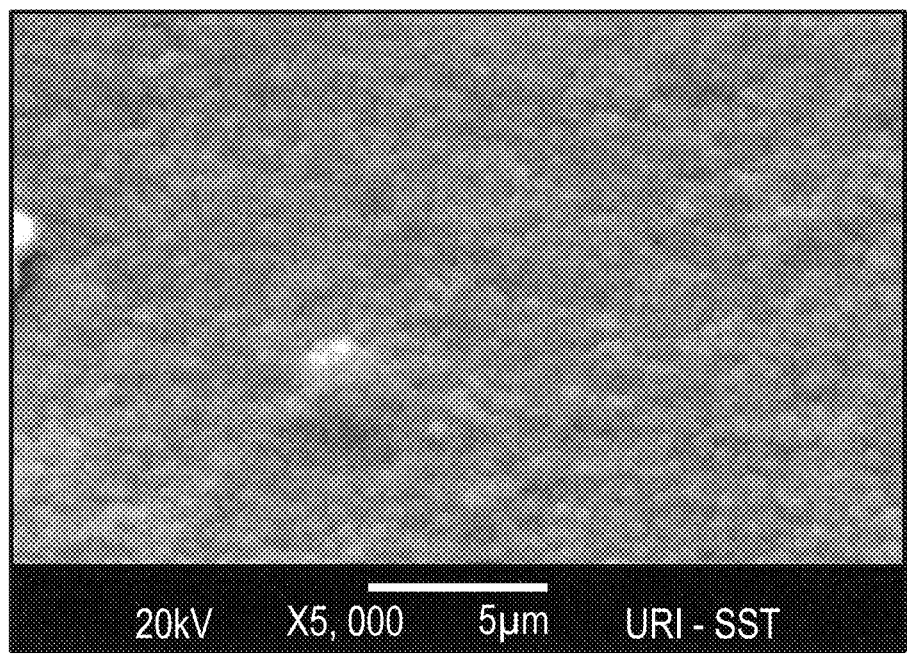
FIG. 7A shows an SEM micrograph of a post-annealed SnO catalyst that was sputtered in 7 mT Ar.
Figure 7B:
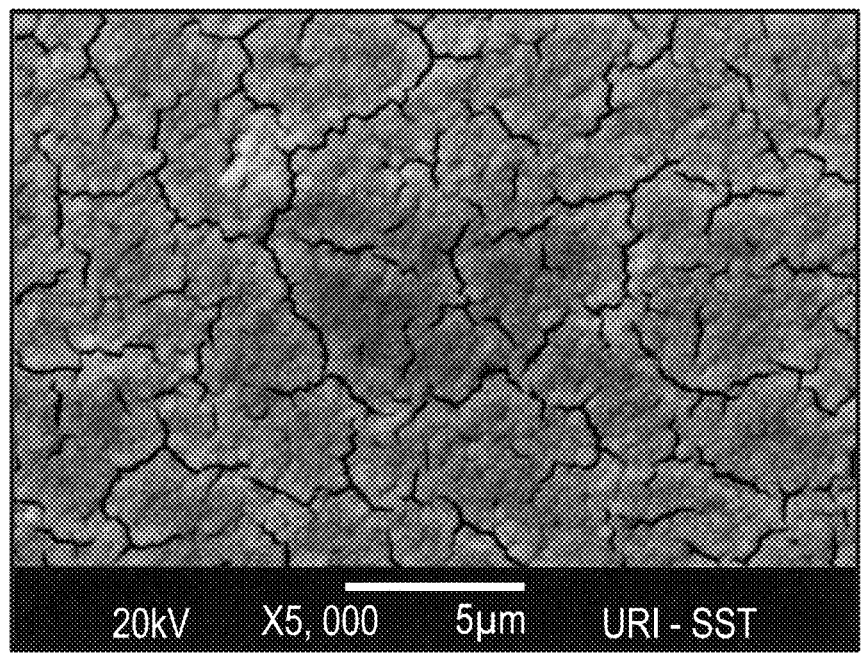
FIG. 7B shows an SEM micrograph of a post-annealed SnO catalyst that was sputtered in 15 mT Ar.

Further optimization of ultrathin vapor sensors in accordance with the present invention was achieved through variation of catalyst porosity. Again, thickness combined with the enhanced catalytic effect associated with the Pd-based microheaters yielded unprecedented sensitivity. Because the ultrathin vapor sensors employ discrete thin films of Pd and SnO, the catalyst porosity played a large role in amplifying the general catalytic properties of the palladium. Porosity in the catalyst was increased by increasing the argon partial pressure during sputtering. Specifically, when the argon partial pressure was increased from 7 mtorr to 15 mtorr, the result was a much greater point defect content (argon trapped in the film). The resulting SnO films were then annealed in nitrogen to release any trapped argon prior to testing. This produced more porosity as the trapped argon diffused out of the film. FIG. 7A depicts a scanning electron microscope (SEM) micrograph of a nitrogen annealed SnO thin film sputtered in 7 mtorr Ar. The resulting film showed typical sputtered protuberances with little porosity. FIG. 7B depicts shows a SEM micrograph of a nitrogen-annealed SnO thin film sputtered in 15 mtorr Ar. This SEM micrograph shows significant microcracking throughout the SnO film, exposing the Pd underneath. These microcracks provide direct access to the Pd-microheater and the TATP vapor, thus permitting simultaneous exposure to the Pd and SnO.

Figure 8:
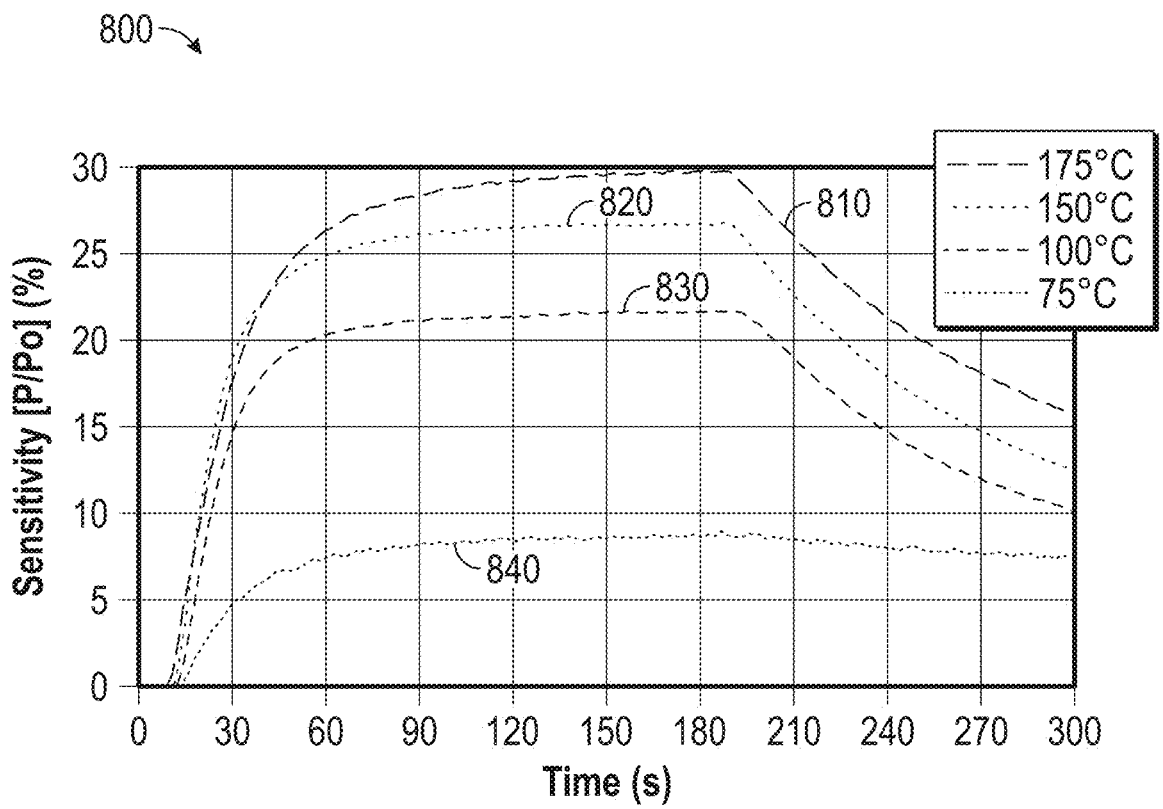
FIG. 8 shows an illustrative graphical representation of a comparison between responses of an ultrathin vapor sensor employing a highly porous SnO catalyst to 20 ppm TATP at a variety of operating temperatures.

FIG. 8 shows comparison 800 of the responses of an ultrathin vapor sensor fabricated on 8 μm YSZ to 20 ppm TATP at a variety of temperatures, specifically 175° C. at line 810, 150° C. at line 820, 100° C. at line 830, and 75° C. at line 840. In the embodiment tested, the sensor showed the best overall sensitivity to TATP. At a temperature of 175° C., the sensor displayed a sensitivity of 30%, which represents a 60-fold increase in sensitivity over the 40 μm YSZ-based platform. In addition, the highly porous SnO catalyst provided greater sensitivity at significantly lower operating temperatures. At 75° C., the sensor displayed a sensitivity of around 9%, which compares favorably to the other YSZ-based platforms. Additionally, the reduction in sensor operating temperature lowered the power requirements significantly so that at 75° C., the sensor required only 150 mW to reach the desired operating temperature. Advantageously, this requirement permits further portability of the sensor platform.

Ultrathin vapor sensors have also been fabricated employing a variety of other metal oxide catalysts. These include aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), and tin oxide (SnO). Each catalyst displays different levels of sensitivity and selectivity based on the chemical reactions that result from the interaction with the target analyte.

Figure 9:
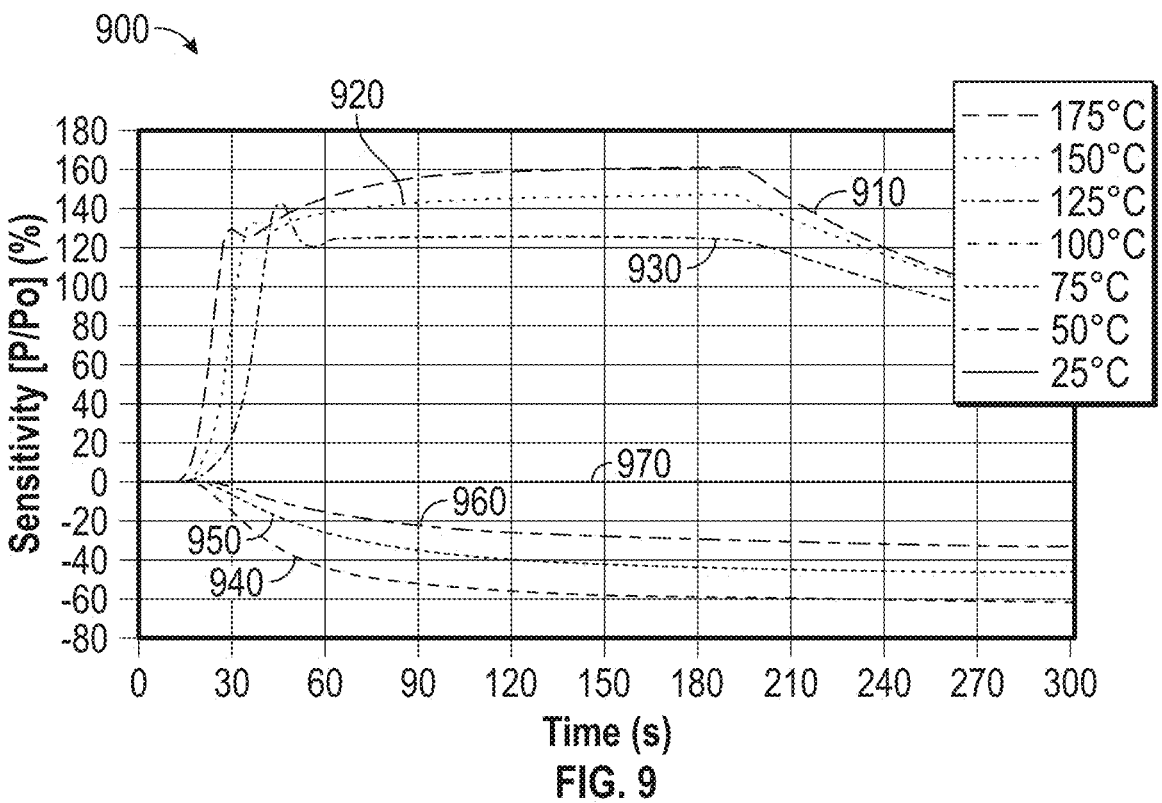
FIG. 9 shows an illustrative graphical representation of a comparison between responses of an ultrathin vapor sensor employing an ITO catalyst to 20 ppm TATP at a variety of operating temperatures.

For example, ITO is a catalyst consisting of highly specific compositions of indium and tin oxide. In reference to FIG. 9, the response of an ultrathin vapor sensor employing a 1.2 μm thick ITO catalyst to 20 ppm TATP at a variety of operating temperatures is described. Specifically, comparison 900 is made between the ultrathin vapor sensor at temperatures of 175° C. at line 910, 150° C. at line 920, 125° C. at line 930, 100° C. at line 940, 75° C. at line 950, 50° C. at line 960, and 25° C. at line 970. At 175° C., the sensor achieved a sensitivity of 160% which represents a 5× increase over a similar sensor employing an SnO catalyst. The sensor also shows improved sensitivity at lower operating temperatures. Based on the properties of the catalyst, at operating temperatures <125° C., the sensor response is negative, which implies that an exothermic reaction has occurred. These reactions release heat resulting in a decrease in required electrical power and thus a negative response. At 100° C., the sensor exhibited a −60% response which is an order of magnitude greater than response exhibited by a SnO catalyst. This improved sensitivity is a result of ITO's high electrical conductivity, which promotes easy transfer of electrons during oxidation and reduction reactions. Catalysts of this type allow for trace detection at the parts-per-trillion (ppt) level using the ultrathin vapor sensors.

Figure 10:
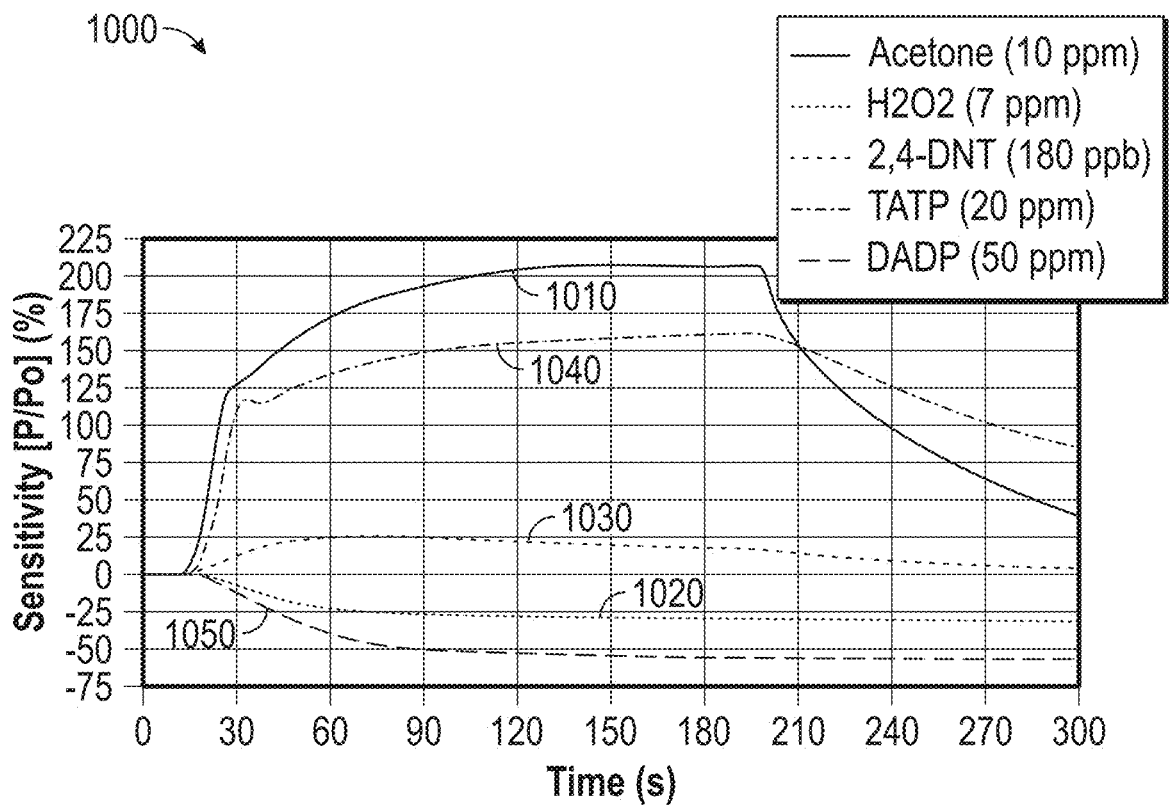
FIG. 10 shows an illustrative graphical representation of a comparison between responses of an ultrathin vapor sensor employing an ITO catalyst to variety of analytes of different vapor pressures at an operating temperature of 175° C.

In addition to unparalleled sensitivity, ITO catalyst also displays improved selectivity. FIG. 10 shows comparison 1000 of responses of an ultrathin vapor sensor employing an ITO catalyst to a variety of analytes, including acetone (10 ppm) at line 1010, $H_2O_2$ (7 ppm) at line 1020, 2,4-DNT (180 ppb) at line 1030, TATP (20 ppm) at line 1040, and diacetone diperoxide (DADP) (50 ppm) at line 1050. Here, the sign and slope of the responses are highly specific toward each analyte. More specifically, ultrathin sensors employing ITO catalysts exhibited a positive (endothermic response) to acetone, TATP, and 2,4-DNT while also exhibiting a negative (exothermic) response to $H_2O_2$ and DADP.

Figure 11:
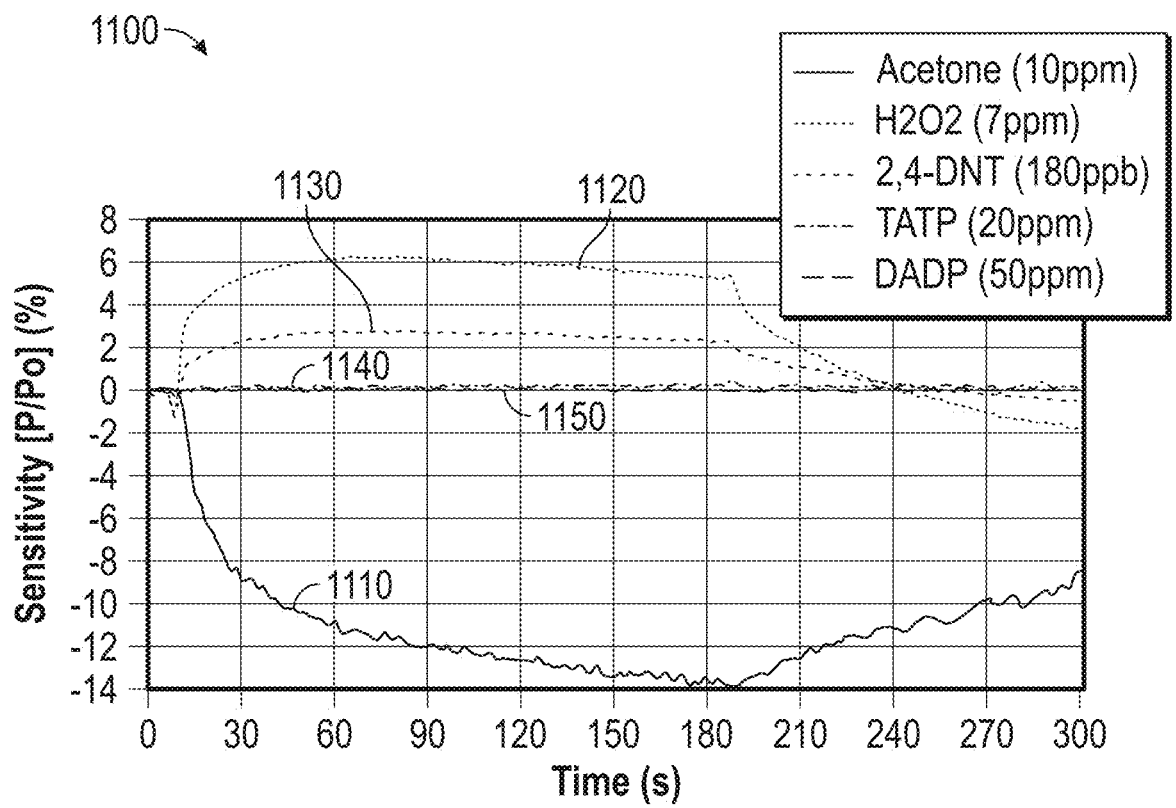
FIG. 11 shows an illustrative graphical representation of a comparison between responses of an ultrathin vapor sensor employing a WO catalyst to variety of analytes of different vapor pressures at an operating temperature of 250° C.

FIG. 11 shows comparison 1100 of responses of an ultrathin vapor sensor employing a WO catalyst to a variety of analytes at an operating temperature of 250° C. The specific analytes are acetone (10 ppm) at line 1110, $H_2O_2$ (7 ppm) at line 1120, 2,4-DNT (180 ppb) at line 1130, TATP (20 ppm) at line 1140, and DADP (50 ppm) at line 1150. Like the ITO catalyst discussed above, WO displays highly selective responses to each analyte. WO shows positive (endothermic) responses to $H_2O_2$ and 2,4-DNT, a negative (exothermic) response to acetone, and is completely inert to TATP and DADP. Similar responses are shown for MnO and $Al_2CuO_4$ (FIGS. 12 and 13 respectively), which are selectivity inert to TATP while also displaying responses to each of the other analytes. These selective responses represent the foundation for a highly selectivity ultrathin vapor sensor array for analyte "fingerprinting."

Figure 12:
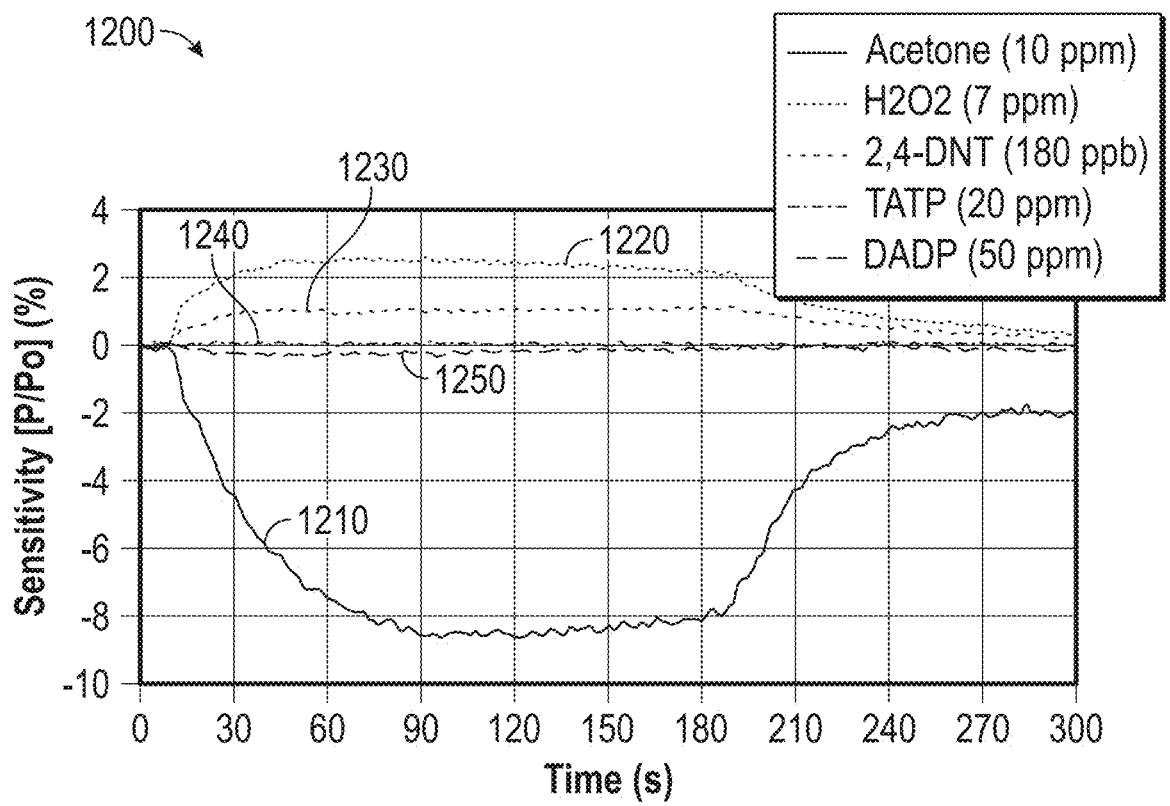
FIG. 12 shows an illustrative graphical representation of a comparison between responses of an ultrathin vapor sensor employing an MnO catalyst to variety of analytes of different vapor pressures at an operating temperature of 250° C.

FIG. 12 depicts comparison 1200 of responses of an ultrathin vapor sensor employing a MnO catalyst to a variety of analytes. The specific analytes are acetone (10 ppm) at line 1210, $H_2O_2$ (7 ppm) at line 1220, 2,4-DNT (180 ppb) at line 1230, TATP (20 ppm) at line 1240, and DADP (50 ppm) at line 1250.

Figure 13:
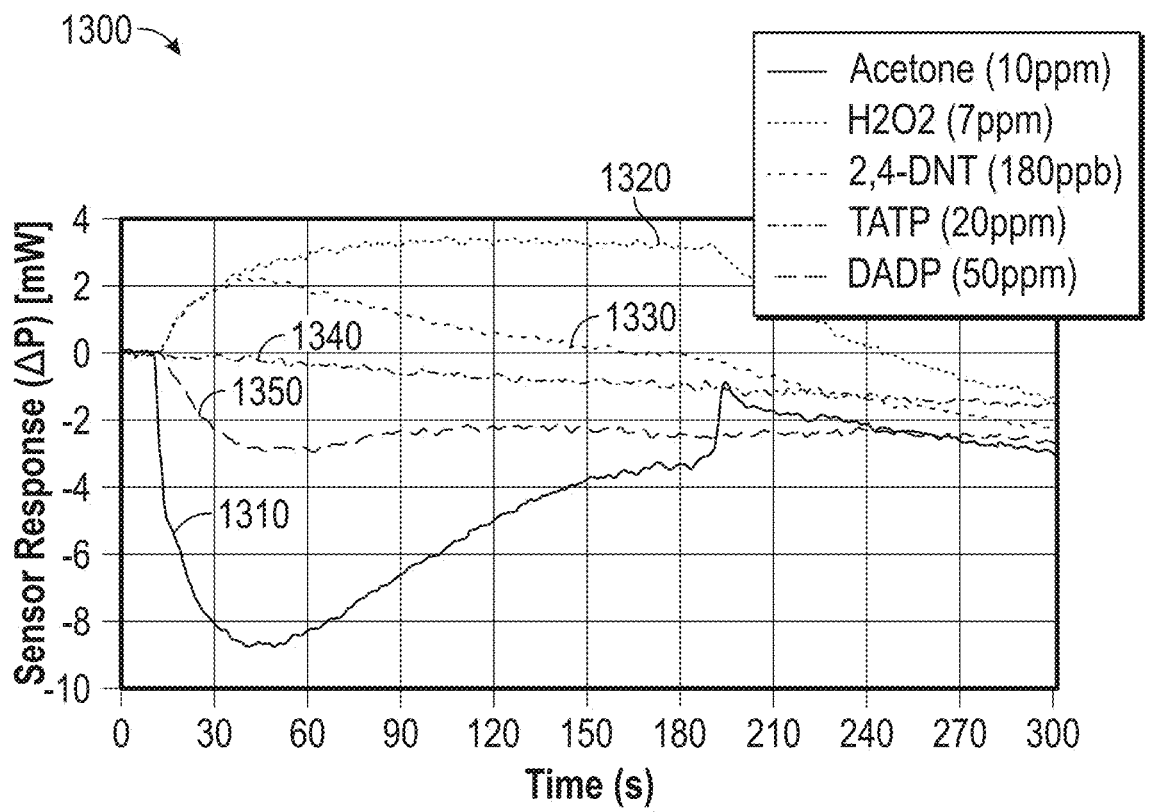
FIG. 13 shows an illustrative graphical representation of a comparison between responses of an ultrathin vapor sensor employing an $Al_2CuO_4$ catalyst to variety of analytes of different vapor pressures at an operating temperature of 250° C.

Likewise, FIG. 13 depicts comparison 1300 of responses of an ultrathin vapor sensor employing a $Al_2CuO_4$ catalyst to a variety of analytes. The specific analytes are acetone (10 ppm) at line 1310, $H_2O_2$ (7 ppm) at line 1320, 2,4-DNT (180 ppb) at line 1330, TATP (20 ppm) at line 1340, and DADP (50 ppm) at line 1350.

Figure 14A:
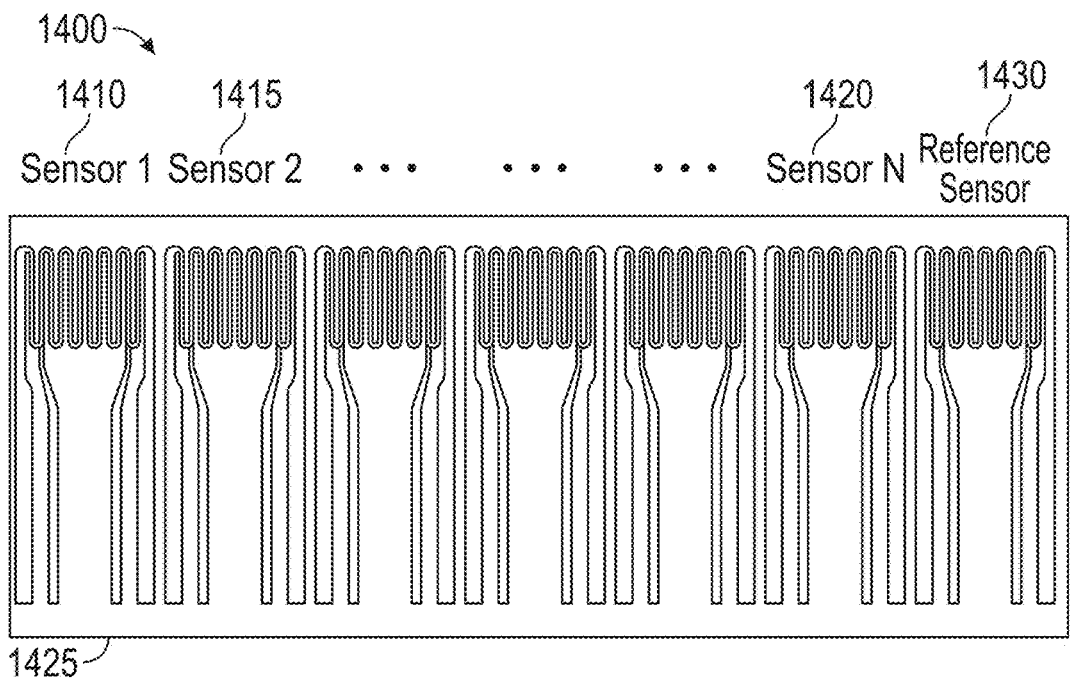
FIGS. 14A and 14B depict embodiments of sensor arrays in which the substrate is shared by the sensors and in which each sensors has an individual substrates, respectively.

Ultrathin vapor sensors in accordance with the present invention are well-suited for an array platform capable of selective detection and identification of a library of vapor phase analytes. The highly anisotropic heating properties allow for easy integration of more than ten or more microheaters (including a reference) on a single substrate with no appreciable thermal communication. An array of this type could be quantitative or qualitative depending on the desired application. It will be appreciated that if a plurality of ultrathin vapor sensors share a common substrate, then the individual substrates of each sensor are contiguous with the substrates of the other commonly mounted sensors. FIG. 14A illustrates an embodiment of sensor array 1400 having N sensors and one reference sensor. Specifically, first sensor 1410, second sensor 1415, and other sensors up to and including Nth sensor 1420 are all mounted on substrate 1425. Reference sensor 1430 is also mounted on substrate 1430.

Figure 14B:
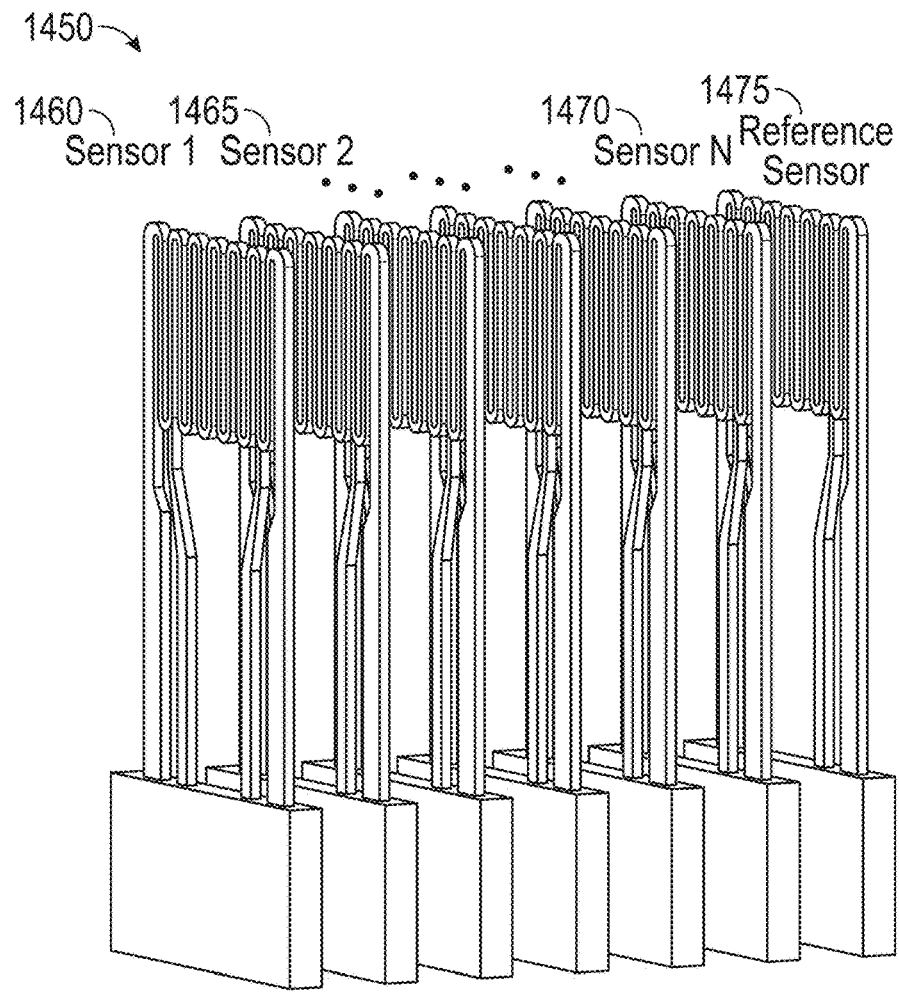

In other preferred embodiments, ultrathin vapor sensors comprise a plurality of microheaters that do not share a common substrate. For example, a device may include a plurality of microheaters (including a reference), each with its own substrate to further prevent thermal communication. FIG. 14B illustrates an embodiment of sensor array 1450 having N sensors and one reference sensor. Specifically, first sensor 1460, second sensor 1465, and other sensors up to and including Nth sensor 1470, as well as reference sensor 1475 each are mounted on separate substrates. It will be appreciated that in embodiments wherein the sensors do not share a common substrate, advantages include increased configuration options, including the ability to position the sensors in different locations relative to one another and facilitated replacement options wherein a subset of a group of sensors may be replaced with other sensors having the same or different catalysts.

Sensor arrays, such as those depicted in FIG. 14A and FIG. 14B, display remarkable flexibly and may be placed in a variety of orientations and at any distance with significantly reduced thermal communication between sensors as compared to known systems. In practice, the controller of the sensor is used to heat each microheater individually to a pre-determined temperature setpoint. Upon or after reaching the desired setpoint temperature, the catalyst coated sensors and reference sensor are exposed to a target analyte, preferably this exposure occurs approximately simultaneously. The individual redox reactions on the surface of each catalyst results in heat effects which are determined by the controller based on the power usage of the sensors. Each measurement is then compared to (e.g., subtracted from) the reference measurement to help mitigate any false positives or false negatives. An array of separate sensors, such as those illustrated in FIG. 14B, could be incorporated into a variety of standalone devices including wearables, breathalyzers, scanning wands, etc. Additionally, the low mass and low power requirements facilitates the use of an array of sensors onboard a variety of mobile platforms including drones, robots, and UAVs.

Upon interaction with the target analyte, each catalyst has the potential for three distinct responses. As mentioned above, reduction reactions produce positive (+) responses while oxidation reactions produce negative (−) responses. A catalyst may also be unresponsive to a target analyte, indicating the absence of any catalytic decomposition/redox reactions and thus, no response (NR). A "fingerprint" may be constructed for each target analyte based on the response of each catalyst. Thus, a set of pre-determined catalysts can be chosen to allow "selective" identification of each analyte.

The sensor arrays depicted in FIG. 14A and FIG. 14B, like other embodiments disclosed herein, may be configured to be quantitative and qualitative as desired. In another embodiments, sensor arrays can measure the magnitude of each thermodynamic response and provide real-time measurement of the analyte concentration in addition to rapid identification of the analyte.

FIG. 15 shows summary table 1500 containing the thermodynamic sign (positive or negative), and thus an indication of the measured redox reactions, for 12 distinct catalysts making up an embodiment of an ultrathin vapor sensor array. The table shows that each of the five analytes (acetone (10 ppm), $H_2O_2$ (7 ppm), TATP (20 ppm), DADP (50 ppm), and 2,4-DNT (180 ppb)) possess distinct "fingerprints" when the reaction results for each of the 12 sensors are compared, and these "fingerprints" may be used for rapid identification. Thus, an ultrathin vapor sensor array formed using some or all of the catalysts in table 1500 could be used to detect an analyte and could identify which of the five analytes was present based on a determination of whether the reaction at individual sensors was endothermic or exothermic and a comparison of the results of the catalysts to the data in summary table 1500. The data in FIG. 15 may be stored in a database accessible by the controller of a sensor array, and the sensor array may compare heat effects of its sensors to the database of known reaction results in order to identify the existence and/or concentration of an analyte. Such as database of reactions results of different catalysts may include an identification of essential and optional catalysts that promote further flexibility of the sensor array platform by allowing configuration to detect one or more specific analytes, such as a group of analytes associated with explosives. The essential catalysts allow for easy identification of the target analyte while the optional catalysts can be added or removed for redundancy. It will be appreciated that the data of summary table 1500 could be expanded through further testing with numerous analytes and the addition of other potential catalysts. Thus the data in the database of summary table 1500 is not limited to the catalysts or analytes identified therein.

Figure 16:
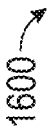
FIG. 16 shows a summary table consisting of the thermodynamic sign indicative of the measured redox reactions, for six catalysts making up an ultrathin vapor sensor array.

The sensor array platform is unique in that the quantity and composition of the catalysts can be modified based on the desired application. In some embodiments, the sensor array can be configured for the detection of explosives and explosive precursors. For example, FIG. 16 depicts table 1600 with data from a database presented in a tabular form illustrating reaction results of a sensor array having of six catalyst sensors (namely, $Al_2CuO_4$, $Fe_2O_3$, ITO, MnO, SnO, and WO). Sensor arrays including these six catalysts are well-suited for selectively identifying analytes having unique "fingerprints" that are identified as being one of least five explosives and two explosive precursors. The number of detectable explosives may be selectively increased through further testing and the addition of more sensors having different catalysts. Sensor arrays that include the catalysts identified in FIG. 16 may be deployed onboard a variety of wearables, vehicles (cars, drones, UAVs), and robots to detect explosives in airports, warzones, or any densely populated venues.

Figure 17:
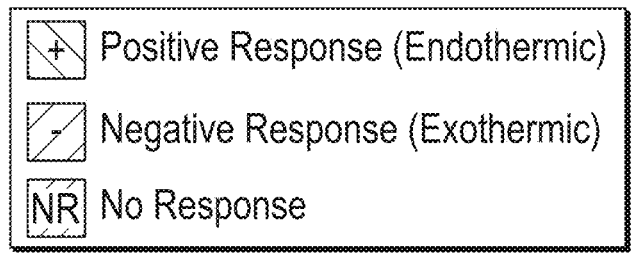
FIG. 17 shows a summary table consisting of the thermodynamic sign indicative of the measured redox reactions, for six catalysts making up an ultrathin vapor sensor array.

In other embodiments, sensor arrays may be configured for the detection of drugs and narcotics as well as hallucinogenic and non-hallucinogenic compounds. FIG. 17 depicts table 1700 with data from a database presented in tabular form illustrating reaction results of a sensor array having six catalysts (namely $Al_2CuO_4$, $Fe_2O_3$, ITO, CuO, SnO, and WO). Sensor arrays that include sensors having these catalysts are well-suited for selectively identifying and differentiating between fentanyl, THC, and CBD, each with unique "fingerprints" as compared to the reaction results with the identified catalysts. Additionally, embodiments of a sensor array having the catalysts identified in FIG. 17 have been shown to detect other drugs (e.g., cocaine) and numerous cannabinoids present in marijuana. Sensor arrays including the catalysts identified in FIG. 17 are well-suited to be deployed by law enforcement in breathalyzers for the detection of THC, as well as by border patrol officers in a scanning wand for the identification of drugs and other illicit materials.

Figure 18:
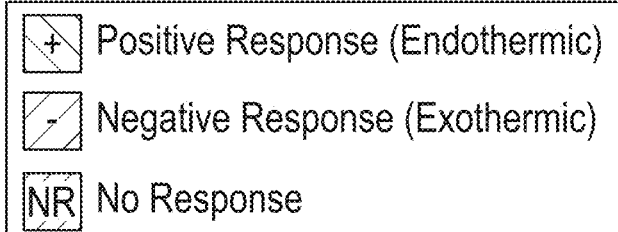
FIG. 18 shows a summary table consisting of the thermodynamic sign indicative of the measured redox reactions, for six catalysts making up an ultrathin vapor sensor array.

In yet other embodiments, sensor arrays may be configured for the detection of biomarkers for known biological functions. FIG. 18 depicts table 1800 with data from a database presented in tabular form illustrating reaction results of a sensor array having six catalysts (namely $Al_2CuO_4$, $Fe_2O_3$, ITO, MnO, SnO, and WO). Sensor arrays that include sensors having these catalysts are well-suited for selectively identifying and differentiating between glucose, fructose, ammonia and $H_2O_2$, thereby providing beneficial diagnostic applications. Glucose vapor has been correlated to blood glucose at known concentrations. Thus, sensor arrays having a configuration of sensors as indicated in FIG. 18 may be deployed as part of a wearable or as a breathalyzer allowing for noninvasive glucose measurement for diabetics. Similarly, ammonia is a known biomarker for chronic kidney disease (CKD). Thus, sensor arrays having a configuration of sensors as indicated in FIG. 18 may be used as part of a breathalyzer for rapid, real-time diagnosis. Moreover, $H_2O_2$ is present is wounds during the healing process. A bandage employing a sensor array having the six catalysts identified in FIG. 18 may measure $H_2O_2$ levels in the wound and provide real-time monitoring of wound healing for first responders.

Figures 19, 20:
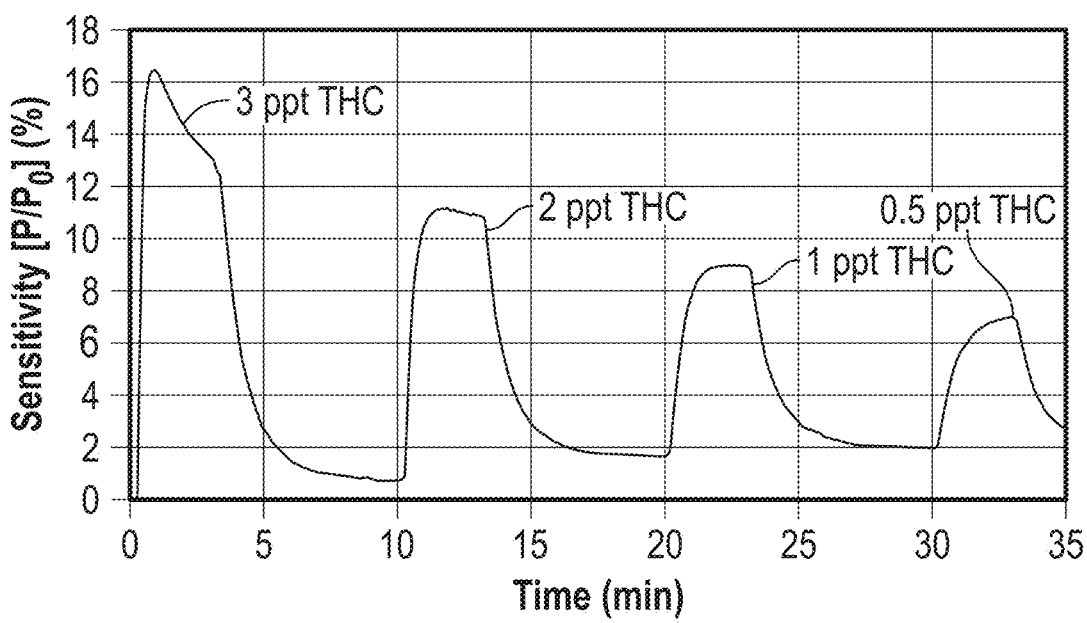
FIG. 19 shows a summary table consisting of the thermodynamic sign indicative of the measured redox reactions, for six catalysts making up an ultrathin vapor sensor array.
FIG. 20 shows an illustrative graphical representation of the response of an ultrathin vapor sensor to tetrahydrocannabinol (THC) at a variety of concentrations using an operating temperature of 175° C.

In yet another embodiments, sensor arrays may be configured for the detection of volatile organic compounds (VOCs) and other industrial compounds. FIG. 19 depicts table 1900 with data from a database presented in tabular form illustrating reaction results of a sensor array having six sensors each with one of the following catalysts: $Al_2CuO_4$, $Fe_2O_3$, ITO, MnO, SnO, and WO. Sensor arrays with such a configuration are well-suited for selectively identifying and differentiating between natural gas, acetone, and methanol. Such sensor arrays may be used, for example, as part of a stationary system for the detection of natural gas leaks in homes and industrial settings.

The tables shown in FIGS. 15-19 depict qualitative examples of data from one or more databases of reaction results of various analytes when exposed to sensors having different catalysts. Such data, when used with a sensor array having sensors with pre-selected catalysts, may be used for the selective identification of analytes by the thermodynamic sensor array. It will be appreciated that the data results identified in these tables represents only a sample of the data collected and that additions to the database may be made through further testing with additional analytes and/or sensors having other catalysts. The tables of FIGS. 15-19 also represent data that may be used (and expanded on) as part of a database for a sensor platform capable of detecting selected analytes.

It will be appreciated that some embodiments of a sensor array may be special purpose detection devices having sensors with catalysts that are selectively chosen to target one or more analytes falling within a certain category (e.g., explosives, drugs and narcotics, biomarkers, etc.). Likewise, other embodiments may contain a larger number of sensors and may be capable of serving as a general purpose detection device, wherein the device may be capable of detecting and differentiating between analytes from a plurality of categories.

Figure 21:
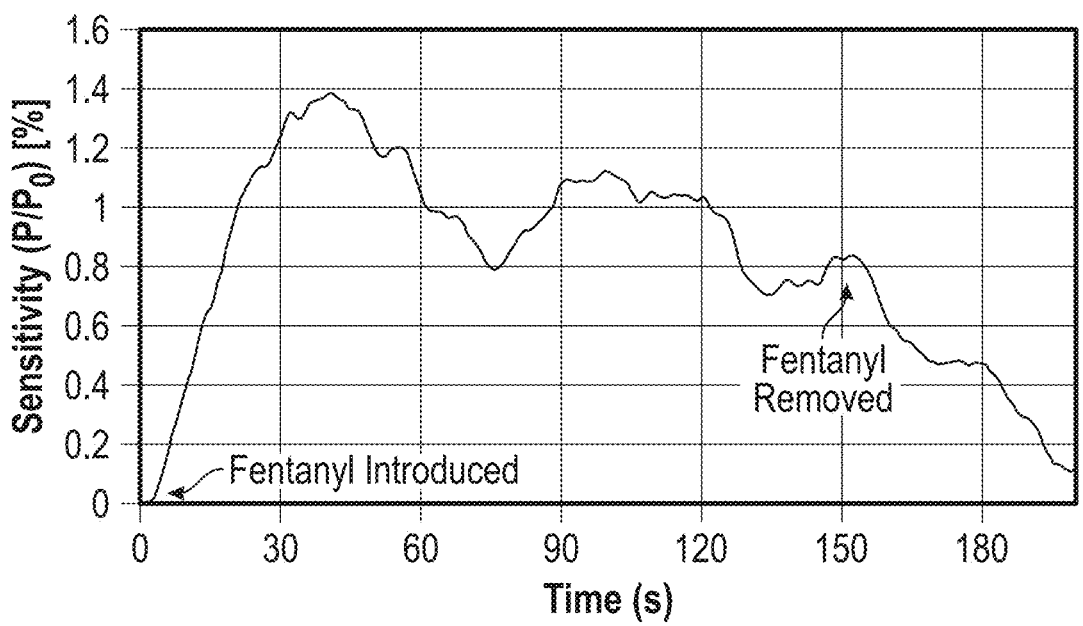
FIG. 21 shows an illustrative graphical representation of the response of an ultrathin vapor sensor to 11 ppt fentanyl using an operating temperature of 175° C.

As mentioned above, the enhanced sensitivity of ultrathin vapor sensor allows for the detection of numerous chemical compounds including explosives, narcotics, pharmacological, and biological compounds. FIG. 20 and FIG. 21 show the response of an ultrathin vapor sensor to tetrahydrocannabinol (THC) and fentanyl respectively. As discussed in reference to FIG. 20, ultrathin vapor sensors of the present invention are capable of detecting THC in the low part-per-trillion levels. One of skill in the art will appreciate that ultrathin vapor sensors disclosed herein could be employed in a variety of law-enforcement or commercial applications for measuring THC levels in a desired search area. This performance has been validated for a variety of vapor phase analytes, as mentioned above. Thus, calibration curves for either increasing or decreasing concentrations may be generated for the precise measurement of the concentration of a target molecule (or analyte) concentration in the vapor phase.

Similarly, as discussed in reference to FIG. 21, ultrathin vapor sensors of the present invention are capable of detecting fentanyl at the ppt level. Accordingly, those of skill in the art will appreciate that these devices allow for real-time, continuous detection of narcotics along borders or other ports-of-entry.

Figure 22:
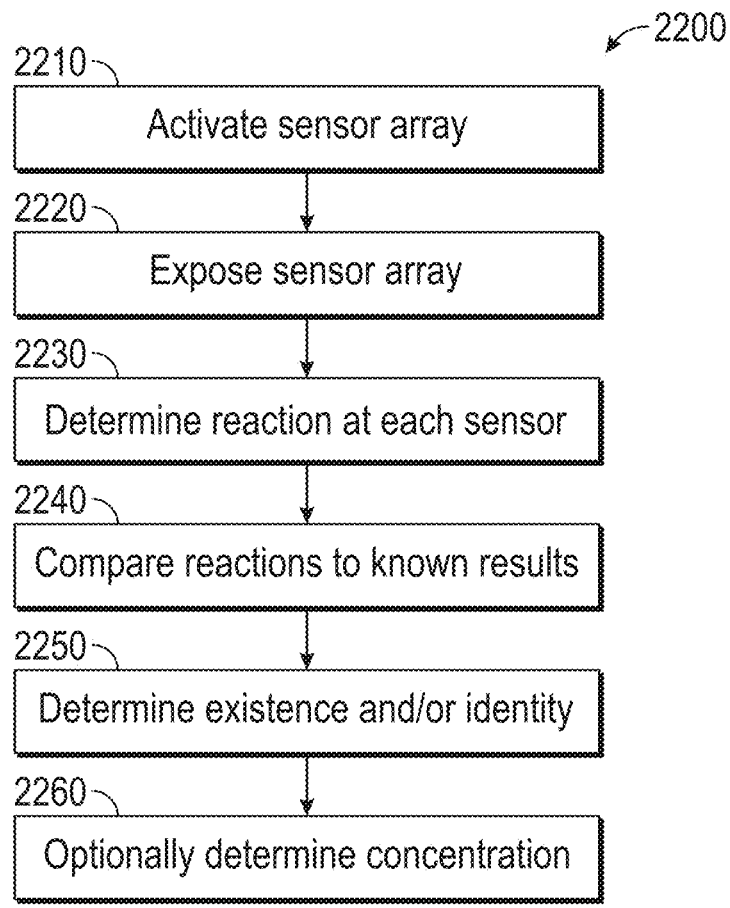
FIG. 22 shows an example of a method of using a sensor array to detect an analyte.

An example of a method of using an embodiment of a sensor array is described in reference to FIG. 22. Method 2200 may be used to determine the existence and/or identity of an analyte and, optionally, the concentration of an analyte. Method 2200 begins at step 2210 in which a user has a sensor array, such as sensor array 1400 or sensor array 1450, each with multiple sensors. The sensor array is activated by providing power to each of the sensors (including one or more reference sensors) so that the temperature of the microheater of each sensor is raised to the desired setpoint temperature. It will be appreciated that each of the sensors need not have the same temperature setpoint, and in operation the sensor array may include sensors operating at different temperature setpoints. In some embodiments, in which the sensors have different setpoint temperatures, a plurality of reference sensors may be provided wherein a reference sensor may be provided for each of the different temperature setpoints and used as a reference point for the sensors having corresponding temperatures. As described herein, the temperature of the sensor may be adjusted through the delivery of power, wherein the addition of power increases the temperature, while the reduction of power lowers the temperature. At step 2220, the sensor array is exposed to an environment in which knowledge of the existence, identity, or concentration of an analyte is desired. For example, the sensor array may be attached to a drone and flown in a battlefield, or mounted in a fixed location at an airport, or provided on a mobile platform that may be worn or carried by a user. When the sensor array is provided in such an environment in which an analyte is present, the analyte reacts with one or more of the sensors in the array.

At step 2230, the reaction at each of the sensors is determined. An exothermic reaction at a sensor will produce heat and the corresponding power required to maintain the sensor at the setpoint temperature will be reduced. Likewise, in response to an endothermic reaction, more power will have to be provided to the sensor to maintain the setpoint temperature. The determination of the reaction at each sensor may be quantitative, in which a determination is made of whether the reaction is endothermic, exothermic, or neither. Additionally, readings of the qualitative magnitude of the power change may be obtained.

At step 2240, the reactions at one or more sensors are compared to known results. In preferred embodiments, the sensor array is in communication with a database of known results and the comparison of the reaction at the sensors to the known results may be automated. At step 2250, a determination is made as to the existence and/or the identity of an analyte based on the comparison of the reaction to the known reaction results. For example, consider a sensor array for detecting drugs configured with the six catalysts corresponding to FIG. 17. If the sensor having the ITO catalyst indicates that an endothermic reaction occurred (requiring the addition of power to maintain the setpoint temperature), a determination may be made that CBD, fentanyl, or THC may be present, as each of these produces an endothermic reaction to the sensor with ITO. However, though the results from that single sensor may indicate the presence of a drug, results from additional sensors are required to identify the analyte. For example, if the sensors having the SnO and WO catalysts each indicate an endothermic reaction, whereas the sensors having the $Al_2CuO_4$, $Fe_2O_3$, and CuO sensors each indicate an exothermic reaction, then a determination may be made that the identity of the analyte is THC. It will be appreciated that due to the "fingerprints" of the various analytes, an identification may be made of some analytes by using less than six sensors.

Some embodiments may include optional step 2260, in which a determination is made of the concentration of the analyte. Here, qualitative data is compared to known results. For example, the change in the power provided to the sensors and the amount of that power may be compared to known results to provide an indication of the concentration of the detected analyte. For example, a rapid change in the power required to operate a sensor may be indicative of a higher concentration of the detected analyte, whereas a more gradual change in the required power is indicative of a lower concentration of the analyte. Graphical results demonstrating the differences in speed and intensity associated with various concentrations of THC are shown in FIG. 20. It will be appreciated that a database of known reaction results could have comparable results with other analytes to which sensor results may be compared to for purposes of determining the concentration of the analyte.

Overall, ultrathin vapor sensors employing ultrathin YSZ substrates and Pd-based microheaters display the ability to detect a multitude of compounds in the vapor at trace levels both continuously and in real-time.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed:

1. A detection device comprising:
a first layer comprising a substrate;
a second layer in contact with the first layer, the second layer comprising an adhesion layer;
a third layer in contact with the second layer, the third layer comprising a metallic microheater configured to receive power at a first power level to reach a setpoint temperature; and
a fourth layer in contact with the third layer, the fourth layer comprising a catalyst configured to undergo a chemical reaction when exposed to an analyte, the chemical reaction being endothermic or exothermic,
wherein the metallic microheater is configured to receive power at a second power level to maintain the setpoint temperature after the catalyst begins the chemical reaction, and
wherein a heat effect indicative of information on the analyte is determined by comparing the second power level to the first power level.

2. The detection device of claim 1, wherein the substrate is yttria-stabilized-zirconia.

3. The detection device of claim 1, wherein the adhesion layer is copper.

4. The detection device of claim 1, wherein the metallic microheater is palladium.

5. The detection device of claim 1, wherein the catalyst is a metal oxide catalyst.

6. The detection device of claim 1, wherein the substrate has a thickness of less than 40 micrometers.

7. The detection device of claim 1, wherein the detection device is further configured to detect the analyte in a vapor phase based on the heat effect.

8. The detection device of claim 7, wherein the detection device is configured to detect the analyte at concentration levels as low as in parts per trillion (ppt).

9. The detection device of claim 1, further comprising a controller configured to cause the power to be provided at the first power level to reach the setpoint temperature, to cause the power to be provided at the second power level to maintain the setpoint temperature after the catalyst begins the chemical reaction, and determine an existence, identity, and/or concentration of the analyte based on comparing the second power level to the first power level.

10. The detection device of claim 1, further comprising a reference sensor that is not coated with a catalyst.

11. The detection device of claim 1, further comprising second sensor comprising a second microheater in thermal communication with a second catalyst different from the first catalyst.

12. The detection device of claim 11, further comprising third, fourth, and fifth sensors comprising third, fourth, and fifth catalysts, respectively.

13. The detection device of claim 12, wherein the first catalyst comprises aluminum copper oxide ($Al_2CuO_4$), the second catalyst comprises iron oxide ($Fe_2O_3$), the third catalyst comprises indium-tin oxide (ITO), the fourth catalyst comprises tin oxide (SnO), and the fifth catalyst comprises tungsten oxide (WO).

14. The detection device of claim 13, further comprising a sixth sensor comprising a sixth catalyst selected from copper oxide (CuO) or manganese oxide (MnO).

15. A detection device comprising:
a first sensor comprising a first microheater and a first catalyst in contact with the first microheater;
a second sensor comprising a second microheater layer and a second catalyst layer in contact with the second microheater layer;
a controller in electrical communication with the first sensor and the second sensor, the controller configured to:

cause power to be provided to the first and second sensors to heat the first sensor to a first setpoint temperature and to heat the second sensor to a second setpoint temperature;

vary power applied to the first sensor and/or the second sensor to account for a thermal response caused by reactions between an analyte and the first catalyst layer and/or the second catalyst layer to maintain the first setpoint temperature and the second setpoint temperature; and determine an existence, identity, and/or concentration of the analyte based on the varied the power.

16. The detection device of claim 15, wherein the first setpoint temperature is the same as the second setpoint temperature.

17. The detection device of claim 15, further comprising a reference sensor comprising a reference microheater and without a catalyst, the reference sensor in electrical communication with the controller.

18. The detection device of claim 15, further comprising a third sensor comprising a third microheater and a third catalyst in thermal communication with the third microheater, a fourth sensor comprising a fourth microheater and a fourth catalyst in thermal communication with the fourth microheater, and a fifth sensor comprising a fifth microheater and a fifth catalyst in thermal communication with the fifth microheater.

19. The detection device of claim 18, wherein the first catalyst comprises aluminum copper oxide ($Al_2CuO_4$), the second catalyst comprises iron oxide ($Fe_2O_3$), the third catalyst comprises indium-tin oxide (ITO), the fourth catalyst comprises tin oxide (SnO), and the fifth catalyst comprises tungsten oxide (WO).

20. The detection device of claim 19, further comprising a sixth sensor comprising a sixth catalyst selected from copper oxide (CuO) or manganese oxide (MnO).

21. The detection device of claim 18, wherein the first catalyst, the second catalyst, the third catalyst, the fourth catalyst, and the fifth catalyst each comprise aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO).

22. The detection device of claim 15, wherein the setpoint temperature is between 50° C. and 500° C.

23. A method of detecting an analyte, the method comprising:

providing a sensor array comprising a first sensor and a second sensor, the first sensor comprising a first microheater layer and a first catalyst layer in contact with the first microheater layer, the second sensor comprising a second microheater layer and a second catalyst layer in contact with the second microheater layer;

delivering power to the first and second sensors to heat the first sensor to a first setpoint temperature and to heat the second sensor to a second setpoint temperature;

exposing the first and second sensors to an analyte such that the first catalyst layer and/or the second catalyst layer react with the analyte to generate a thermal response;

varying power applied to the first sensor and/or the second sensor to account for the thermal response to maintain the first setpoint temperature and the second setpoint temperature; and determining an existence, identity, and/or concentration of the analyte based on varying the power.

24. The method of claim 23, wherein the first setpoint temperature and the second setpoint temperature are each between 50° C. and 500° C.

25. The method of claim 23, wherein determining an existence, identity, and/or concentration of the analyte based on varying the power further comprises comparing the thermal response to a database of known thermal responses.

26. The method of claim 23, wherein the sensor array further comprises a reference sensor and wherein determining the existence, identity, and/or concentration of the analyte comprises analyzing information on power supplied to the reference sensor.

27. The method of claim 23, wherein the first catalyst layer comprises aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO).

28. The method of claim 27, wherein the second catalyst layer comprises aluminum copper oxide ($Al_2CuO_4$), aluminum zinc oxide (AZO), chromium oxide ($CrO_2$), copper oxide (CuO), cobalt oxide ($CoO_2$), iron oxide ($Fe_2O_3$), indium-tin oxide (ITO), iridium oxide ($IrO_2$), manganese oxide (MnO), ruthenium oxide ($RuO_2$), tungsten oxide (WO), or tin oxide (SnO).

* * * * *